United States Patent
Ee et al.

(10) Patent No.: US 11,993,801 B2
(45) Date of Patent: May 28, 2024

(54) BASE-MODIFIED NUCLEOTIDES AS SUBSTRATES FOR TDT-BASED ENZYMATIC NUCLEIC ACID SYNTHESIS

(71) Applicants: Illumina Singapore Pte. Ltd., Singapore (SG); Nanyang Technological University, Singapore (SG)

(72) Inventors: Pin Koon Ee, Singapore (SG); Yin Nah Teo, Singapore (SG); Shunsuke Chiba, Singapore (SG)

(73) Assignees: Illumina Singapore Pte. Ltd., Singapore (SG); Nanyang Technological University, Singapore (SG)

( * ) Notice: Subject to any disclaimer, the term of this patent is extended or adjusted under 35 U.S.C. 154(b) by 121 days.

(21) Appl. No.: 17/381,024

(22) Filed: Jul. 20, 2021

(65) Prior Publication Data

US 2022/0025421 A1  Jan. 27, 2022

Related U.S. Application Data

(60) Provisional application No. 63/054,766, filed on Jul. 21, 2020.

(51) Int. Cl.
 *C12P 19/34* (2006.01)
 *C12N 9/12* (2006.01)

(52) U.S. Cl.
 CPC ............ *C12P 19/34* (2013.01); *C12N 9/1264* (2013.01); *C12Y 207/07031* (2013.01)

(58) Field of Classification Search
 CPC ..... C12P 19/34; C12N 9/1264; C12Q 1/6806; C12Q 2521/131; C12Q 2523/319
 USPC ..... 435/6.1, 91.1, 91.31, 455, 458; 536/23.1
 See application file for complete search history.

(56) References Cited

U.S. PATENT DOCUMENTS

| | | | |
|---|---|---|---|
| 10,059,929 | B2 | 8/2018 | Efcavitch et al. |
| 10,583,415 | B2 | 3/2020 | Banyai et al. |
| 2009/0280535 | A1 | 11/2009 | Wang |
| 2018/0023108 | A1 | 1/2018 | Chen et al. |
| 2019/0390178 | A1 | 12/2019 | Champion et al. |
| 2021/0009969 | A1 | 1/2021 | Tubbs et al. |
| 2021/0355460 | A1 | 11/2021 | Nirantar et al. |
| 2021/0355518 | A1 | 11/2021 | Nirantar et al. |

FOREIGN PATENT DOCUMENTS

| | | |
|---|---|---|
| GB | 2553274 | 3/2018 |
| WO | WO2004018497 | 3/2004 |
| WO | WO2014162307 | 10/2014 |
| WO | WO2016064880 | 4/2016 |
| WO | WO2016128731 | 8/2016 |
| WO | WO2017216472 | 12/2017 |
| WO | WO2018217689 | 11/2018 |
| WO | WO2020081985 | 4/2020 |
| WO | WO2020161480 | 8/2020 |
| WO | WO2021116270 | 6/2021 |
| WO | WO2021231477 | 11/2021 |
| WO | WO2021231483 | 11/2021 |

OTHER PUBLICATIONS

Deshpande et al., "Enzymatic synthesis and modification of high molecular weight DNA using terminal deoxynucleotidyl transferase," Methods Enzymol 2019, 627, 163-188.
Final Office Action dated Oct. 12, 2022 in U.S. Appl. No. 17/317,721.
Guo et al., "Protein tolerance to random amino acid change," PNAS 2004, 101(25), 9205-9210.
Hayes et al., "Combining computational and experimental screening for rapid optimization of protein properties," PNAS 2002, 99(25), 15926-15931.
Ngo et al., "Computational Complexity, Protein Structure Prediction, and the Levinthal Paradox," The Protein Folding Problem and Tertiary Structure Prediction 1994, 492-495.
Non-final Office Action dated May 16, 2022 in U.S. Appl. No. 17/317,721.
Baranello et al., "DNA Break Mapping Reveals Topoisomerase II Activity Genome-Wide," International Journal of Molecular Sciences 2014, 15, 13111-13122.
Barthel et al., "Enhancing Terminal Deoxynucleotidyl Transferase Activity on Substrates with 3′ Terminal Structures for Enzymatic De Novo DNA Synthesis," Genes 2020, 11(102), in 9 pages.
Beaucage & Caruthers, "Deoxynucleoside Phosphoramidites—A New Class Of Key Intermediates For Deoxypolynucleotide Synthesis," Tetrahedron Letters 1981, 22(20), 1859-1862.
Bentley et al., "Accurate whole human genome sequencing using reversible terminator chemistry," Nature 2008, 456, in 7 pages.
Bertocci et al., "Nonoverlapping Functions of DNA Polymerases Mu, Lambda, and Terminal Deoxynucleotidyltransferase during Immunoglobulin V(D)J Recombination In Vivo," Immunity 2006, 25, 31-41.
Bollum et al., "Thermal Conversion of Nonpriming Deoxyribonucleic Acid to Primer," The Journal of Biological Chemistry 1959, 234(10), 2733-2734.
Bollum et al., "Calf Thymus Polymerase," The Journal of Biological Chemistry 1960, 235(8), 2399-2403.
Bollum, "Terminal Deoxynucleotidyl Transferase," The Enzymes 1974, 10, 145-171.
Bornholt et al., "A DNA-Based Archival Storage System," ASPLOS 2016, 637-649.
Boule et al., "Comparison of the Two Murine Deoxynucleotidyltransferase Terminal Isoforms," The Journal of Biological Chemistry 2000, 275(37), 28984-28988.

(Continued)

*Primary Examiner* — Jane J Zara
(74) *Attorney, Agent, or Firm* — Sheppard, Mullin, Richter & Hampton LLP

(57) ABSTRACT

Disclosed herein include methods and compositions for nucleic acid synthesis using a terminal deoxynucleotidyl transferase with deoxyribonucleotide trisphosphates each comprising a modified base with a photocleavable carbon chain moiety that enables single incorporations when present.

22 Claims, 9 Drawing Sheets

Specification includes a Sequence Listing.

(56) References Cited

OTHER PUBLICATIONS

Bowers et al., "Virtual Terminator nucleotides for next generation DNA sequencing," Nat Methods 2009, 6(8), 593-595.
Caruthers, "The Chemical Synthesis of DNA/RNA: Our Gift to Science," The Journal of Biological Chemistry 2013, 288(2), 1420-1427.
Chen et al., "The History and Advances of Reversible Terminators Used in New Generations of Sequencing Technology," Genomics Proteomics Bioinformatics 2013, 11, 34-40.
Chua et al., "Evolving a Thermostable Terminal Deoxynucleotidyl Transferase," ACS Synthetic Biology 2020, 9, 1725-1735.
Church et al., "Next-Generation Digital Information Storage in DNA," Sciencexpress 2012, in 2 pages.
Delarue et al., "Crystal structures of a template-independent DNA polymerase: murine terminal deoxynucleotidyltransferase," The EMBO Journal 2002, 21(3), 427-439.
Durowoju et al., "Differential Scanning Calorimetry—A Method for Assessing the Thermal Stability and Conformation of Protein Antigen," Journal of Visualized Experiments 2017, 121, in 8 pages.
Dymond et al., "Synthetic chromosome arms function in yeast and generate phenotypic diversity by design," Nature 2013, 477(7365), 471-476.
Extance, "Digital DNA; Could the Molecule known for storing genetic information also store the world's data?" Nature 2016, 537, 22-24.
Gavrieli et al., "Identification of Programmed Cell Death In Situ via Specific Labeling of Nuclear DNA Fragmentation," The Journal of Cell Biology 1992, 119(3), 493-501.
Gibson et al., "Creation of a Bacterial Cell Controlled by a Chemically Synthesized Genome," Science 2010, 329(5987), 52-56.
Goldman et al., "Toward practical high-capacity low-maintenance storage of digital information in synthesized DNA," Nature 2013, 494(7435), 77-80.
Gorczyca et al., "Detection of DNA Strand Breaks in Individual Apoptic Cells by in Situ Terminal Deoxynucleotidyl Transferase and Nick Translation Assays," Cancer Research 1993, 53, 1945-1951.
Hottin & Marx, "Structural Insights into the Processing of Nucleobase-Modified Nucleotides by DNA Polymerases," American Chemical Society 2016, 49, 418-427.
Hu et al., "A TdT-mediated cascade signal amplification strategy based on dendritic DNA matrix for label-free multifunctional electrochemical biosensing," Biosensors and Bioelectronics 2015, 63, 331-338.
Hutchinson et al., "Design and synthesis of a minimal bacterial genome," Science 2016, 351(6280), in 12 pages.
Hutter et al., "Labeled Nucleoside Triphosphates With Reversibly Terminating Aminoalkoxyl Groups," Nucleosides, Nucleotides and Nucleic Acids 2010, 29, 879-895.
Huynh and Partch, "Analysis of protein stability and ligand interactions by thermal shift assay," Current Protocols in Protein Science 2015, 79, in 19 pages.
International Search Report and Written Opinion dated Aug. 26, 2021 in PCT Patent Application No. PCT/US2021/031852.
International Search Report and Written Opinion dated Nov. 11, 2021 in PCT Patent Application No. PCT/US2021/031843.
Jarchow-Choy et al., "Fluorescent xDNA nucleotides as efficient substrates for a template-independent polymerase," Nucleic Acids Research 2011, 39(4), 1586-1894.
Jensen & Davis, "Template-Independent Enzymatic Oligonucleotide Synthesis (TiEOS): Its History, Prospects, and Challenges," Biochemistry 2018, in 12 pages.
Ju et al., "Four-color DNA sequencing by synthesis using cleavable fluorescent nucleotide reversible terminators," PNAS 2006, 103(52), 19635-19640.
Juárez et al., "A specific loop in human DNA polymerase mu allows switching between creative and DNA-instructed synthesis," Nucleic Acids Research 2006, 34(16), 4572-4582.
Kato et al., "Deoxynucleotide-polmerizing Enzymes of Calf Thymus Gland," The Journal of Biological Chemisty 1987, 242(11), 2780-2789.
Kelley et al., "The Phyre2 web portal for protein modelling, prediction and analysis," Nature Protocols 2015, 10(6), 845-858.
Lazinski & Camilli, "Homopolymer tail-mediated ligation PCR: a streamlined and highly efficient method for DNA cloning and library construction," BioTechniques 2013, 54(1), 25-34.
Lee et al., "Terminator-free template-independent enzymatic DNA synthesis for digital information storage," Nature Communications 2019, 10(2283), in 12 pages.
Lee et al., "Enzymatic DNA synthesis for digital information storage," bioRxiv 2018, in 31 pages.
Leproust et al., "Synthesis of high-quality libraries of long (150mer) oligonucleotides by a novel depurination controlled process," Nucleic Acids Research 2010, 38(8), 2522-2540.
Liang et al., "Synthetic biology: putting synthesis into biology," WIREs Syst Biol Med 2011, 3, 7-20.
Loc'h et al., "Structural evidence for an in trans base selection mechanism involving Loop1 in polymerase µ at an NHEJ double-strand break junction," The Journal of Biological Chemistry 2019, 294(27), 10579-10595.
Loc'h , "Terminal deoxynucleotidyltransferase: the story of an untemplated DNA polymerase capable of DNA bridging and templated synthesis across strands," Current Opinion in Structural Biology 2018, 53, 22-31.
Moon et al., "The X Family Portrait: Structural Insights into Biological Functions of X Family Polymerases," DNA Repair 2007, 6(12), 1709-1725.
Motea & Berdis, "Terminal Deoxynucleotidyl Transferase: The Story of a Misguided DNA Polymerase," Biochimica et Biophysica Acta 2010, 1804(5), 1151-1166.
Musil et al., "FireProt: web server for automated design of thermostable proteins," Nucleic Acids Research 2017, 45, W393-W399.
Ostrov et al., "Design, synthesis, and testing toward a 57-codon genome," Science 2016, 353(6301), 819-822.
Palluk et al., "De novo DNA synthesis using polymerase-nucleotide conjugates," Nature Biotechnology 2018, 1-6.
Peng et al., "TELP, a sensitive and versatile library construction method for next-generation sequencing," Nucleic Acids Research 2014, 43(6), e35, in 13 pages.
Pina-Anguilar et al., "Revival of Extinct Species Using Nuclear Transfer: Hope for the Mammoth, True for the Pyrenean Ibex, But Is It Time for "Conservation Cloning"?," Cloning and Stem Cells 2009, 11(3), in 6 pages.
Richardson et al., "Design of a synthetic yeast genome," Science 2017, 355, 1040-1044.
Romain et al., "Conferring a template-dependent polymerase activity to terminal deoxynucleotidyltransferase by mutations in the Loop1 region," Nucleic Acids Research 2009, 37(14), 4642-4656.
Rosa et al., "Meltdown: A Tool to Help in the Interpretation of Thermal Melt Curves Acquired by Differential Scanning Fluorimetry," Journal of Biomolecular Screening 2015, 20(7), 898-905.
Ruparel et al., "Design and synthesis of a 3'-O-allyl photocleavable fluorescent nucleotide as a reversible terminator for DNA sequencing by synthesis," PNAS 2005, 102(17), 5932-5937.
Sarac & Hollenstein, "Terminal Deoxynucleotidyl Transferase in the Synthesis and Modification of Nucleic Acids," ChemBioChem 2019, 20, 860-871.
Sharma et al., "Terminal deoxynucleotidyl transferase dUTP nick end labeling (TUNEL) assay using bench top flow cytometer for evaluation of sperm DNA fragmentation in fertility laboratories: protocol, reference values, and quality control," The Journal of Assisted Reproduction and Genetics 2016, 33, 291-300.
Slavíčková et al., "Additions of Thiols to 7-Vinyl-7-deazaadenine Nucleosides and Nucleotides. Synthesis of Hydrophobic Derivatives of 2'-Deoxyadenosine, dATP and DNA," The Journal of Organic Chemistry 2016, 81, 11115-11125.
Tauraitė et al., "Modified Nucleotides as Substrates of Terminal Deoxynucleotidyl Transferase," Molecules 2017, 22(672), in 16 pages.

(56) References Cited

OTHER PUBLICATIONS

Tjong et al., "Amplified On-Chip Fluorescence Detection of DNA Hybridization by Surface-Initiated Enzymatic Polymerization," Analytical Chemistry 2011, 5153-5159.
Tjong et al., Direct Fluorescence Detection of RNA on Microarrays by Surface-Initiated Enzymatic Polymerization, Analytical Chemistry 2013, 85, 426-433.
Woolly Mammoth Revival, "Why Bring Back the Woolly Mammoth?" Revive & Restore 2021, in 3 pages. http://reviverestore.org/projects/woolly-mammoth/.
Yang et al., "Mutational Analysis of Residues in the Nucleotide Binding Domain of Human Terminal Deoxynucleotidyl Transferase," The Journal of Biological Chemistry 1994, 269(16), 11859-11868.
Yazdi et al., "Portable and Error-Free DNA-Based Data Storage," Scientific Reports 2017, 7(5011), 1-6.
International Search Report and Written Opinion dated Jan. 24, 2022 in PCT Patent Application No. PCT/US2021/031843.
Jena Bioscience, "Azide-PEG4-aminoallyl-dUTP Data Sheet", 2020, in 1 page.
Restriction Requirement dated Feb. 22, 2022 in U.S. Appl. No. 17/317,721.
Sørensen et al., "Enzymatic Ligation of Large Biomolecules to DNA", ACS Nano 2013, 7(9), 8098-8104.
Winz et al., "Site-specific one-pot triple click labeling for DNA and RNA", Chemical Communications 2018, 54(83), 11781-11784.

SEQUENCE LISTING

<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 1
attcaggacg agcctcagac c    21

BASE-MODIFIED NUCLEOTIDES AS SUBSTRATES FOR TDT-BASED ENZYMATIC NUCLEIC ACID SYNTHESIS

CROSS-REFERENCE TO RELATED APPLICATIONS

This application claims the benefit of priority to U.S. Provisional Patent Application No. 63/054,766, filed Jul. 21, 2020, the content of which is incorporated herein by reference in its entirety.

REFERENCE TO SEQUENCE LISTING

The present application is being filed along with a Sequence Listing in electronic format. The Sequence Listing is provided as a file entitled Sequences_Listing_47CX-311972-US, created Jul. 6, 2021, which is 1 kilobyte in size. The information in the electronic format of the Sequence Listing is incorporated herein by reference in its entirety.

BACKGROUND

Field

The present disclosure relates generally to the field of nucleic acid synthesis, for example using base-modified nucleotides for TdT-based nucleic acid synthesis.

Description of the Related Art

Deoxyribonucleic acid (DNA) is traditionally synthesized using a four-step chemical method based on phosphoramidite chemistry, allowing synthesis of DNA strands up to 250-300 base pairs. Enzymatic gene synthesis is an alternative to achieve the synthesis of DNA sequences.

SUMMARY

Disclosed herein include embodiments of a method of nucleic acid synthesis. In some embodiments, the method comprises (a1) providing a nucleic acid, a first nucleoside triphosphate, and a first terminal deoxynucleotidyl transferase (TdT), the first nucleoside triphosphate comprises a modified base comprising a photocleavable carbon chain moiety having a length of at least 60 Å. The method can comprise: (b1) contacting (i) the nucleic acid and (ii) the first nucleoside triphosphate with the first TdT to generate a first modified nucleic acid comprising the nucleic acid incorporated with one first nucleotide comprising the modified base from the first nucleoside triphosphate. The method can comprise (c1) photocleaving the photocleavable carbon chain moiety of the modified base of the first nucleotide in the first modified nucleic acid to remove the photocleavable carbon chain moiety from the first modified nucleic acid.

In some embodiments, the method further comprises: (a2) providing a second nucleoside triphosphate and a second TdT, the second nucleoside triphosphate comprises a modified base comprising a photocleavable carbon chain moiety having a length of at least 60 Å. The method can comprise: (b2) contacting (i) the first modified nucleic acid with the photocleavable carbon chain moiety of the modified base of the first nucleotide removed and (ii) the second nucleoside triphosphate with the second TdT to generate a second modified nucleic acid comprising the first modified nucleic acid incorporated with one second nucleotide comprising the modified base from the second nucleoside triphosphate. The method can comprise (c2) photocleaving the photocleavable carbon chain moiety of the modified base of the second nucleotide in the second modified nucleic acid to remove the photocleavable carbon chain moiety from the second modified nucleic acid.

Disclosed herein include embodiments of a method of nucleic acid synthesis. In some embodiments, the method comprises: (a) providing a nucleic acid and a plurality of nucleoside triphosphates, each of the plurality of nucleoside triphosphates comprises a modified base comprising a photocleavable carbon chain moiety having a length of at least 60 Å. The method can comprise (b1) contacting (i) the nucleic acid and (ii) a first nucleoside triphosphate of the plurality of nucleoside triphosphates with a first terminal deoxynucleotidyl transferase (TdT) to generate a first modified nucleic acid comprising the nucleic acid incorporated with one first nucleotide comprising the modified base from the first nucleoside triphosphate. The method can comprise (c1) photocleaving the photocleavable carbon chain moiety of the modified base of the first nucleotide in the first modified nucleic acid to remove the photocleavable carbon chain moiety from the first modified nucleic acid. The method can comprise (b2) contacting (i) the first modified nucleic acid with the photocleavable carbon chain moiety of the modified base of the first nucleotide removed and (ii) a second nucleoside triphosphate of the plurality of nucleoside triphosphates with a second TdT to generate a second modified nucleic acid comprising the first modified nucleic acid incorporated with one second nucleotide comprising the modified base from the second nucleoside triphosphate. The method can comprise (c2) photocleaving the photocleavable carbon chain moiety of the modified base of the second nucleotide in the second modified nucleic acid to remove the photocleavable carbon chain moiety from the second modified nucleic acid.

In some embodiments, a concentration of the nucleic acid is at least 10 nM. In some embodiments, the nucleic acid comprises a single-stranded (ss) nucleic acid. In some embodiments, the nucleic acid comprises a deoxyribonucleic acid (DNA). In some embodiments, the nucleic acid comprises at least one ribonucleotide. In some embodiments, the nucleic acid is attached to a solid support. In some embodiments, the solid support comprises a flow cell surface. In some embodiments, the method further comprises: detaching the modified nucleic acid from the solid support.

In some embodiments, a concentration of the first nucleoside triphosphate and/or the second nucleoside triphosphate is at least 0.1 µM. In some embodiments, the modified base comprises a modified cytosine, a modified uracil, a modified thymine, a modified adenine, or a modified guanine. In some embodiments, the modified base comprises a propargylamino group, an aminoallyl group, a propargylhydroxyl group or a combination thereof.

In some embodiments, the photocleavable carbon chain moiety comprises a saturated or unsaturated, substituted or unsubstituted, straight or branched carbon chain. In some embodiments, the carbon chain has a length of at least 60 Å. In some embodiments, the photocleavable carbon chain moiety comprises at least 54 carbon, oxygen, nitrogen, and/or sulfur atoms in a main chain of the carbon chain. In some embodiments, the photocleavable carbon chain moiety comprises a plurality of repeat units. In some embodiments, the plurality of repeating units comprises identical repeating units. In some embodiments, one of the plurality of repeating units comprises at least three carbon, oxygen, nitrogen, and/or sulfur atoms in a main chain of the repeating unit. In some embodiments, the plurality of repeating units comprises a polyethylene glycol (PEG). In some embodiments, a repeating unit of the plurality of repeating units comprises no aromatic group. In some embodiments, a repeating unit of the plurality of repeating units comprises an aromatic group. In some embodiments, a number of the plurality of repeating units is at least 18.

In some embodiments, the photocleavable carbon chain moiety comprises a photocleavable moiety selected from a group consisting of a carbonyl group, an arylcarbonylmethyl group, a phenacyl group, an o-alkylphenacyl group, a p-hydroxyphenacyl group, a benzoin group, a benzyl group, a nitroaryl group, a nitrobenzyl group, an o-nitrobenzyl group, an o-nitro-2-phenethyloxycarbonyl group, an o-nitroanilide, a coumarin-4-ylmethyl group, an arylmethyl group, a coumaryl group, an o-hydroxyarylmethyl group, a metal-containing group, a pivaloyl group, an ester of a carboxylic acid, an arylsulfonyl group, a ketone group, a carbanion-mediated group, a sisyl group, a silicon-based group, a 2-hydroxycinnamyl group, an α-keto amide group, an α,β-unsaturated anilide, a methyl(phenyl)thiocarbamic acid group, a thiochromone S,S-dioxide group, 2-pyrrolidino-1,4-benzoquinone group, a triazine group, an arylmethyleneimino group, a xanthene group, a pyronin group, a 7-hydroxy-1,1-dimethylnaphthalenone group, a carboxylic acid group, a phosphate group, a phosphite group, a sulfate group, an acid group, an alcohol group, a thiol group, a N-oxide group, a phenol group, an amine group, a derivative of any of the proceeding, or a combination thereof.

In some embodiments, a concentration of the first TdT and/or the second TdT is at least 10 nM. In some embodiments, the first TdT and/or the second TdT comprises a recombinant TdT. In some embodiments, the first TdT and the second TdT are identical. In some embodiments, the first TdT and the second TdT comprise identical molecules of a TdT. In some embodiments, the first TdT and the second TdT comprise different molecules of a TdT. In some embodiments, the first TdT and the second TdT are different TdTs. In some embodiments, the method further comprises: removing the first TdT after the step (b1) and before the step (c1); and removing the second TdT after the step (b2) and before the step (c2). In some embodiments, the first TdT is attached to a first bead, removing the first TdT comprises magnetically removing the first TdT after the step (b1) and before the step (c1), the second TdT is attached to a second bead, and removing the second TdT comprises magnetically removing the second TdT after the step (b2) and before the step (c2). In some embodiments, the first magnetic bead and the second magnetic bead are identical. In some embodiments, the method further comprises: inactivating the first TdT after the step (b1) and before the step (c1); and inactivating the second TdT after the step (b2) and before the step (c2). In some embodiments, inactivating the first TdT comprises heat inactivating the first TdT, and inactivating the second TdT comprises heat inactivating the second TdT.

In some embodiments, the contacting in step (b1) is performed for about 5 minutes to about 20 minutes. The contacting in step (b2) can be performed for about 5 minutes to about 20 minutes. In some embodiments, the contacting in step (b1) is performed at about 16° C. to about 58° C. The contacting step (b2) can be performed at about 16° C. to about 58° C.

In some embodiments, the first modified nucleic acid in step (b1) comprises at least 95% of the nucleic acid. The second modified nucleic acid in step (b2) can comprise at least 95% of the first modified nucleic acid. In some embodiments, at least 95% of the first modified nucleic acid in step (b1) comprises the first modified nucleic acid comprising the nucleic acid incorporated with a single first nucleotide from the first nucleoside triphosphate. At least 95% of the second modified nucleic acid in step (b2) can comprise the second modified nucleic acid comprising the first modified nucleic acid incorporated with a single second nucleotide from the second nucleoside triphosphate.

In some embodiments, the photocleaving in step (c1) is performed with a first radiation. The photocleaving in step (c2) can be performed with a second radiation. In some embodiments, the first radiation and/or the second radiation has a wattage of about 5 watts to about 20 watts. In some embodiments, the first radiation and/or the second radiation comprises an ultraviolet (UV) radiation. In some embodiments, the first radiation and/or the second radiation has a wavelength of about 300 nm to about 400 nm. In some embodiments, the first radiation and/or the second radiation is generated using an ultraviolet (UV) lamp with a wattage of about 10 watts to about 60 watts. In some embodiments, the photocleaving in step (c1) and/or the photocleaving in step (c2) is performed for about 1 minute to about 20 minutes. In some embodiments, the photocleaving in the step (c1) and/or the step (c2) has an efficiency of at least 90%.

In some embodiments, the contacting in step (b1) and the contacting in step (b2) each is completed in about 7 minutes. In some embodiments, the photocleaving in step (c1) and the photocleaving in step (c2) each is completed in about 1 minute. In some embodiments, the contacting in step (b1) and the photocleaving in step (c1) are completed in about 10 minutes, and the contacting in step (b2) and the photocleaving in step (c2) are completed in about 10 minutes.

In some embodiments, the method further comprises: generating a reverse complement of the modified nucleic acid using a polymerase.

Disclosed herein include embodiments of a method of nucleic acid synthesis. In some embodiments, the method comprises: (a1) providing a nucleic acid. The method can comprise: iteratively, (a2) providing a nucleoside triphosphate of a plurality of nucleoside triphosphates and a terminal deoxynucleotidyl transferase (TdT), the nucleoside triphosphate comprises a modified base comprising a photocleavable carbon chain moiety having a length of at least 60 Å; (b) contacting (i) the nucleic acid in (a1) for a first iteration, or the modified nucleic acid in (c) from an immediate prior iteration for any iteration other than the first iteration, and (ii) the nucleoside triphosphate with the TdT to generate a modified nucleic acid comprising the nucleic acid in (a1) for the first iteration, or the modified nucleic acid in (c) from an immediate prior iteration for any iteration other than the first iteration, incorporated with one nucleotide comprising the modified base from the nucleoside triphosphate; and (c) photocleaving the photocleavable carbon chain moiety of the modified base of the nucleotide in the modified nucleic acid to remove the photocleavable carbon chain moiety from the modified nucleic acid. The method can generate the modified nucleic acid comprising a predetermined sequence.

In some embodiments, at least 95% of the modified nucleic acid generated after a plurality of iterations comprises the predetermined sequence. In some embodiments, the plurality of iterations comprises at least 200 iterations. In some embodiments, the method comprises: receiving the predetermined sequence.

Disclosed herein include embodiments of a plurality of nucleoside triphosphates for nucleotide synthesis a terminal deoxynucleotidyl transferase (TdT). Each of the plurality of nucleotide triphosphate can comprise a modified base, the modified base comprises a photocleavable carbon chain moiety having a length of at least 60 Å.

In some embodiments, the modified base comprises a modified cytosine, a modified uracil, a modified thymine, a modified adenine, or a modified guanine. In some embodiments, the modified base comprises a propargylamino group, an aminoallyl group, or a combination thereof.

In some embodiments, the photocleavable carbon chain moiety comprises a saturated or unsaturated, substituted or unsubstituted, straight or branched carbon chain. In some embodiments, the carbon chain has a length of at least 60 Å. In some embodiments, the photocleavable carbon chain moiety comprises at least 54 carbon, oxygen, nitrogen, and/or sulfur atoms in a main chain of the carbon chain. In some embodiments, the photocleavable carbon chain moiety comprises a plurality of repeat units. In some embodiments, the plurality of repeating units comprises identical repeating units. In some embodiments, one of the plurality of repeating units comprises at least three carbon, oxygen, nitrogen, and/or sulfur atoms in a main chain of the repeating unit. In some embodiments, the plurality of repeating units comprises a polyethylene glycol (PEG). In some embodiments, a repeating unit of the plurality of repeating units comprises no aromatic group. In some embodiments, a repeating unit of the plurality of repeating units comprises an aromatic group. In some embodiments, a number of the plurality of repeating units is at least 18.

In some embodiments, the photocleavable carbon chain moiety comprises a photocleavable moiety selected from a group consisting of a carbonyl group, an arylcarbonylmethyl group, a phenacyl group, an o-alkylphenacyl group, a p-hydroxyphenacyl group, a benzoin group, a benzyl group, a nitroaryl group, a nitrobenzyl group, an o-nitrobenzyl group, an o-nitro-2-phenethyloxycarbonyl group, an o-nitroanilide, a coumarin-4-ylmethyl group, an arylmethyl group, a coumaryl group, an o-hydroxyarylmethyl group, a metal-containing group, a pivaloyl group, an ester of a carboxylic acid, an arylsulfonyl group, a ketone, a carbanion-mediated group, a sisyl group, a silicon-based group, a 2-hydroxycinnamyl group, an α-keto amide, an α,β-unsaturated anilide, a methyl(phenyl)thiocarbamic acid, a thiochromone S,S-dioxide, 2-pyrrolidino-1,4-benzoquinone group, a triazine group, an arylmethyleneimino group, a xanthene group, a pyronin group, a 7-hydroxy-1,1-dimethylnaphthalenone, a carboxylic acid, a phosphate, a phosphite, a sulfate, an acid, an alcohol, a thiol, a N-oxide, a phenol, an amine, a derivative of any of the proceeding, or a combination thereof.

In some embodiments, the photocleavable moiety is photocleavable by a radiation with a wattage of about 5 watts to about 20 watts in about 1 minute to about 20 minutes with an efficiency of at least 90%. In some embodiments, the radiation comprises an ultraviolet (UV) radiation. In some embodiments, the radiation has a wavelength of about 300 nm to about 400 nm.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

Figure 1A:
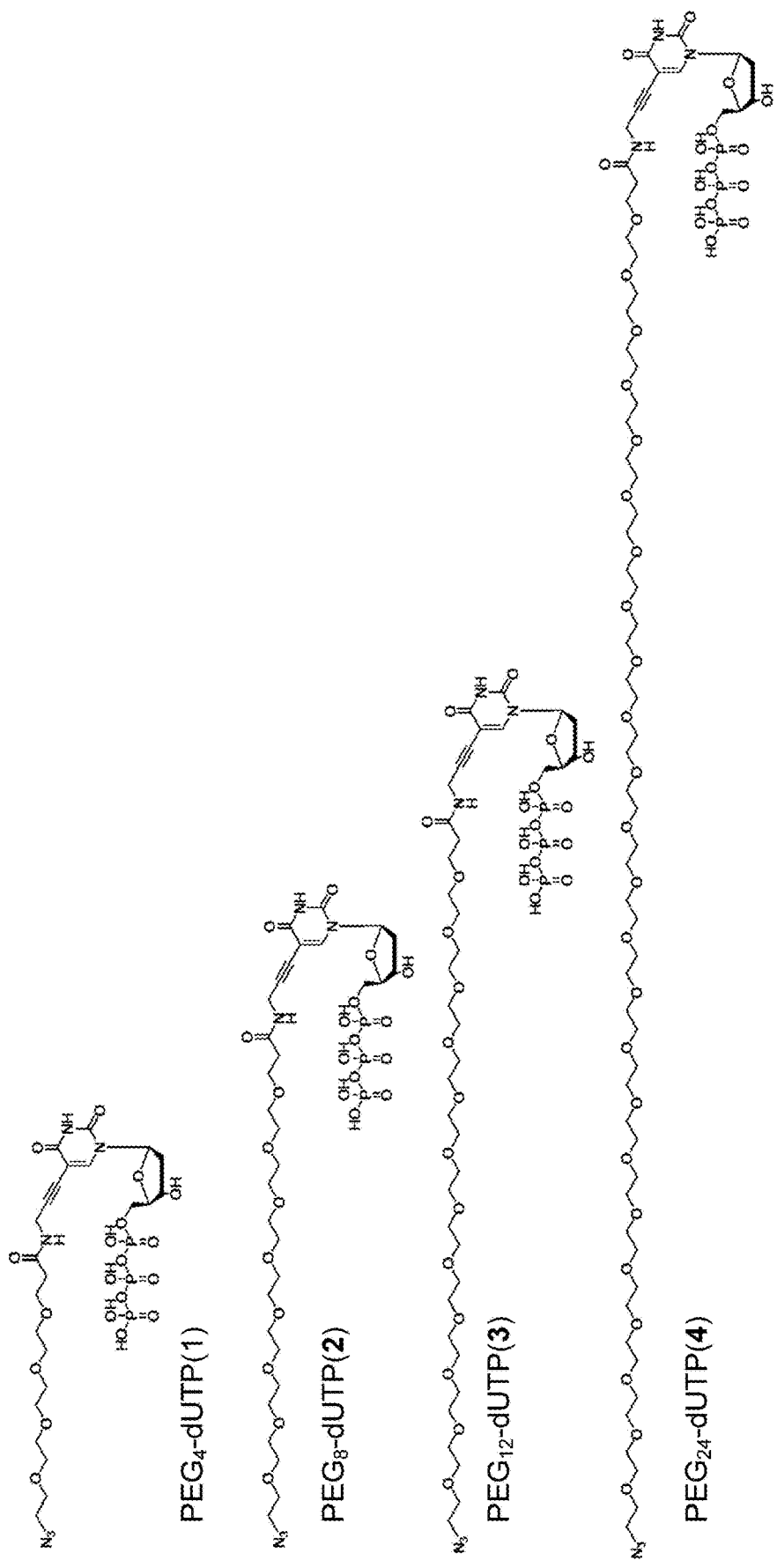
FIG. 1A. Structures of nucleotides 1-4.

Throughout the drawings, reference numbers may be re-used to indicate correspondence between referenced elements. The drawings are provided to illustrate example embodiments described herein and are not intended to limit the scope of the disclosure.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Traditionally, DNA has been synthesized using a four-step chemical method based on phosphoramidite chemistry. By controlling depurination, the synthesis of oligonucleotides 250-300 nucleotides in length can be achieved. Enzymatic gene synthesis, for example, using terminal deoxynucleotidyl transferase (TdT) is an alternative to achieve the synthesis of DNA sequences.

The TdT enzyme, also known as the misguided polymerase, is a unique polymerase as TdT does not require a template strand for oligonucleotide synthesis. Since TdT can incorporate nucleotides indiscriminately, TdT can be used to achieve enzymatic gene synthesis. However, TdT incorporates more than 8000 bases over 24 hours when unmodified nucleotides are used. For TdT to be useful in enzymatic gene synthesis, TdT can perform a single incorporation every time a specific nucleotide is introduced. Such single incorporation allows the exact sequence of the DNA oligonucleotide desired to be synthesized. If multiple incorporations occur every time a specific nucleotide is introduced, there will not be control in the sequence synthesized.

There are two possible strategies to achieve controlled single incorporation events with TdT. The 3' hydroxyl (3'-OH) group of the nucleotide can be modified with a reversible blocking group, or the nucleobase can be modified with a reversible blocking group that prevents more than one incorporation. These reversible blocks can then be removed after the incorporation event, to allow the next incorporation to occur.

The use of 3' hydroxyl blocking groups on the nucleotides requires engineering of the natural TdT polymerase to accommodate the larger 3' block in the enzyme active site. Modification of human TdT at the nucleotide binding domain may result in significant loss of activity and stability. Only 3-16% of TdT's activity was retained when residues near the nucleotide binding side were mutated. TdT has been evolved in an attempt to incorporate 3'-blocked nucleotides.

The second strategy to achieve single incorporation events is to have the blocking group at the nucleobase, while keeping the 3' hydroxyl position unblocked. Modifications at the 3' hydroxyl group directly impact the enzyme active site. However, modifications at the C5-position of pyrimidines or the C7-position of 7-deazapurines of nucleotides extend away from the enzyme active site and are more tolerated by polymerases. The development of the nucleobase modification that can block subsequent incorporations involves nucleotide engineering to optimize the size and attributes such as lipophilicity of the blocking group. In addition, the modified nucleotide should be efficiently incorporated by TdT, as well as block subsequent incorporations after its incorporation.

Disclosed herein include embodiments of a method of nucleic acid synthesis. In some embodiments, the method comprises (a1) providing a nucleic acid, a first nucleoside triphosphate, and a first terminal deoxynucleotidyl transferase (TdT), the first nucleoside triphosphate comprises a modified base comprising a photocleavable carbon chain moiety having a length of at least 60 Å. The method can comprise: (b1) contacting (i) the nucleic acid and (ii) the first nucleoside triphosphate with the first TdT to generate a first modified nucleic acid comprising the nucleic acid incorporated with one first nucleotide comprising the modified base from the first nucleoside triphosphate. The method can comprise (c1) photocleaving the photocleavable carbon chain moiety of the modified base of the first nucleotide in the first modified nucleic acid to remove the photocleavable carbon chain moiety from the first modified nucleic acid.

Disclosed herein include embodiments of a method of nucleic acid synthesis. In some embodiments, the method comprises: (a) providing a nucleic acid and a plurality of nucleoside triphosphates, each of the plurality of nucleoside triphosphates comprises a modified base comprising a photocleavable carbon chain moiety having a length of at least 60 Å. The method can comprise (b1) contacting (i) the nucleic acid and (ii) a first nucleoside triphosphate of the plurality of nucleoside triphosphates with a first terminal deoxynucleotidyl transferase (TdT) to generate a first modified nucleic acid comprising the nucleic acid incorporated with one first nucleotide comprising the modified base from the first nucleoside triphosphate. The method can comprise (c1) photocleaving the photocleavable carbon chain moiety of the modified base of the first nucleotide in the first modified nucleic acid to remove the photocleavable carbon chain moiety from the first modified nucleic acid. The method can comprise (b2) contacting (i) the first modified nucleic acid with the photocleavable carbon chain moiety of the modified base of the first nucleotide removed and (ii) a second nucleoside triphosphate of the plurality of nucleoside triphosphates with a second TdT to generate a second modified nucleic acid comprising the first modified nucleic acid incorporated with one second nucleotide comprising the modified base from the second nucleoside triphosphate. The method can comprise (c2) photocleaving the photocleavable carbon chain moiety of the modified base of the second nucleotide in the second modified nucleic acid to remove the photocleavable carbon chain moiety from the second modified nucleic acid.

Disclosed herein include embodiments of a method of nucleic acid synthesis. In some embodiments, the method comprises: (a1) providing a nucleic acid. The method can comprise: iteratively, (a2) providing a nucleoside triphosphate of a plurality of nucleoside triphosphates and a terminal deoxynucleotidyl transferase (TdT), the nucleoside triphosphate comprises a modified base comprising a photocleavable carbon chain moiety having a length of at least 60 Å; (b) contacting (i) the nucleic acid in (a1) for a first iteration, or the modified nucleic acid in (c) from an immediate prior iteration for any iteration other than the first iteration, and (ii) the nucleoside triphosphate with the TdT to generate a modified nucleic acid comprising the nucleic acid in (a1) for the first iteration, or the modified nucleic acid in (c) from an immediate prior iteration for any iteration other than the first iteration, incorporated with one nucleotide comprising the modified base from the nucleoside triphosphate; and (c) photocleaving the photocleavable carbon chain moiety of the modified base of the nucleotide in the modified nucleic acid to remove the photocleavable carbon chain moiety from the modified nucleic acid. The method can generate the modified nucleic acid comprising a predetermined sequence.

Disclosed herein include embodiments of a plurality of nucleoside triphosphates for nucleotide synthesis a terminal deoxynucleotidyl transferase (TdT). Each of the plurality of nucleotide triphosphate can comprise a modified base, the modified base comprises a photocleavable carbon chain moiety having a length of at least 60 Å.

Enzymatic Nucleic Acid Synthesis

Deoxyribonucleic acid (DNA) can be synthesized using a four-step chemical method based on phosphoramidite chemistry, allowing synthesis of DNA strands up to 250-300 base pairs. Enzymatic gene synthesis is an alternative to achieve the synthesis of DNA sequences, such as long DNA sequences. The Terminal Deoxynucleotidyl Transferase (TdT) is a template-independent DNA polymerase that can be used for such enzymatic based gene synthesis. In order to achieve incorporation of a single nucleotide at a time with TdT, a reversible blocking group can be present either at the 3' hydroxyl position of the nucleotide or at the nucleobase.

Two Incorporation Reactions and Photocleavage Reactions

Disclosed herein include methods of nucleic acid synthesis. In some embodiments, a method of nucleic acid synthesis comprises: (a) providing a nucleic acid and a plurality of nucleoside triphosphates. Each of the plurality of nucleoside triphosphates can comprise a modified base. The modified base can comprise a photocleavable carbon chain moiety having a length of at least 30 Å.

$n^{th}$ Incorporation Reaction and Photocleavage Reaction. The method can comprise (b1) contacting (i) the nucleic acid and (ii) a first nucleoside triphosphate of the plurality of nucleoside triphosphates with a first terminal deoxynucleotidyl transferase (TdT) to generate a first modified nucleic acid. The first modified nucleic acid can comprise the nucleic acid incorporated with one first nucleotide comprising the modified base from the first nucleoside triphosphate. The method can comprise (c1) photocleaving the photocleavable carbon chain moiety of the modified base of the first nucleotide in the first modified nucleic acid to remove the photocleavable carbon chain moiety from the first modified nucleic acid.

$(n+1)^{th}$ Incorporation Reaction and Photocleavage Reaction. The method can comprise (b2) contacting (i) the first modified nucleic acid with the photocleavable carbon chain moiety of the modified base of the first nucleotide removed and (ii) a second nucleoside triphosphate of the plurality of nucleoside triphosphates with a second TdT to generate a second modified nucleic acid. The second modified nucleic acid can comprise the first modified nucleic acid incorporated with one second nucleotide comprising the modified base from the second nucleoside triphosphate. The method can comprise (c2) photocleaving the photocleavable carbon chain moiety of the modified base of the second nucleotide in the second modified nucleic acid to remove the photocleavable carbon chain moiety from the second modified nucleic acid.

Multiple Incorporation Reactions and Photocleavage Reactions

In some embodiments, a method of nucleic acid synthesis comprises (a1) providing a nucleic acid. The method can comprise iteratively, (a2) providing a nucleoside triphosphate of a plurality of nucleoside triphosphates and a terminal deoxynucleotidyl transferase (TdT), the nucleoside triphosphate comprises a modified base comprising a photocleavable carbon chain moiety having a length of at least 30 Å. The method can comprise (b) contacting (i) the nucleic acid in (a1) for a first iteration, or the modified nucleic acid in (c) from an immediate prior iteration for any iteration other than the first iteration, and (ii) the nucleoside triphosphate with the TdT to generate a modified nucleic acid comprising the nucleic acid in (a1) for the first iteration, or the modified nucleic acid in (c) from an immediate prior iteration for any iteration other than the first iteration, incorporated with one nucleotide comprising the modified base from the nucleoside triphosphate. The method can comprise (c) photocleaving the photocleavable carbon chain moiety of the modified base of the nucleotide in the modified nucleic acid to remove the photocleavable carbon chain moiety from the modified nucleic acid. The method can generate the modified nucleic acid comprising a predetermined sequence. The method can comprise: receiving the predetermined sequence.

Different percentages of the modified nucleic acid generated after a plurality of iterations can comprise the predetermined sequence. The number of the plurality of iterations can be different in different embodiments. In some embodiments, the number of iterations comprises, comprises about, comprises at least, comprises at least about, comprises at most, or comprises at most about, 10, 20, 30, 40, 50 60, 70, 80, 90, 100, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 7000, 8000, 9000, 10000, or a number or a range between any two of these values. For example, the plurality of iterations comprises at least 200 iterations.

Removing TdT

In some embodiments, the method comprises removing the TdT used after an incorporation reaction or contacting step and before a photocleavage step. For example, the method comprises removing the first TdT after the step (b1) and before the step (c1). As another example, the method can comprise removing the second TdT after the step (b2) and before the step (c2). In some embodiments, the first TdT is attached to a first magnetic bead or particle. Removing the first TdT can comprise magnetically removing the first TdT after the step (b1) and before the step (c1). The second TdT can be attached to a second magnetic bead or particle. Removing the second TdT can comprise magnetically removing the second TdT after the step (b2) and before the step (c2). In some embodiments, the first magnetic bead and the second magnetic bead are identical. In some embodiments, the first TdT and the second TdT are identical. In some embodiments, the first TdT and the second TdT comprise an identical molecule of a TdT. In some embodiments, the first TdT and the second TdT comprise different molecules of a TdT.

Inactivating TdT

In some embodiments, the method comprises inactivating the TdT used after an incorporation reaction or contacting step and before a photocleavage step. For example, the method can comprise inactivating the first TdT after the step (b1) and before the step (c1). The method can comprise inactivating the second TdT after the step (b2) and before the step (c2). In some embodiments, inactivating the first TdT comprises heat inactivating the first TdT, Inactivating the second TdT can comprise heat inactivating the second TdT.

Nucleic Acid

The concentration of the nucleic acid can be different in different embodiments. In some embodiments, the concentration of the nucleic acid is, is about, is at least, is at least about, is at most, or is at most about, 0.1 nM, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, 1 µM, 2 µM, 3 µM, 4 µM, 5 µM, 6 µM, 7 µM, 8 µM, 9 µM, 10 µM, 20 µM, 30 µM, 40 µM, 50 µM, 60 µM, 70 µM, 80 µM, 90 µM, 100 µM, or a number or a range between any two of these values. For example, the concentration of the nucleic acid is at least 10 nM.

In some embodiments, the nucleic acid comprises a single-stranded (ss) nucleic acid. In some embodiments, the nucleic acid comprises a double stranded (ds) nucleic acid with a 3' overhang. In some embodiments, the nucleic acid comprises a double stranded nucleic acid with a 3' recess. In some embodiments, the nucleic acid comprises a deoxyribonucleic acid (DNA). In some embodiments, the nucleic acid comprises at least one ribonucleotide.

In some embodiments, the nucleic acid is attached to a solid support. The nucleic acid can be attached to the solid support covalently or non-covalently. The nucleic acid can be attached to the solid support directly or indirectly. The nucleic acid can be conjugated to the solid support. The solid support can be or comprise a bead or a particle. The solid support can be non-magnetic, magnetic, or paramagnetic. The solid support can be or comprise a flow cell surface. In some embodiments, the method comprises: detaching the modified nucleic acid from the solid support.

Nucleoside Triphosphate

The concentration of a nucleoside triphosphate of the present disclosure (e.g., the first nucleoside triphosphate, and the second nucleoside triphosphate) can be different in different embodiments. In some embodiments, the concentration of the nucleoside triphosphate is, is about, is at least, is at least about, is at most, or is at most about, 0.001 µM, 0.002 µM, 0.003 µM, 0.004 µM, 0.005 µM, 0.006 µM, 0.007 µM, 0.008 µM, 0.009 µM, 0.01 µM, 0.02 µM, 0.03 µM, 0.04 µM, 0.05 µM, 0.06 µM, 0.07 µM, 0.08 µM, 0.09 µM, 0.1 µM, 0.2 µM, 0.3 µM, 0.4 µM, 0.5 µM, 0.6 µM, 0.7 µM, 0.8 µM, 0.9 µM, 1 µM, 2 µM, 3 µM, 4 µM, 5 µM, 6 µM, 7 µM, 8 µM, 9 µM, 10 µM, 20 µM, 30 µM, 40 µM, 50 µM, 60 µM, 70 µM, 80 µM, 90 µM, 100 µM, or a number or a range between any two of these values. For example, the concentration of the nucleoside triphosphate is at least 0.1 µM.

Base

In some embodiments, the modified base comprises a modified cytosine (C), a modified uracil (U), a modified thymine (T), a modified adenine (A), or a modified guanine (G). In some embodiments, the modified base comprises a propargylamino group, an aminoallyl group, a propargylhydroxyl group or a combination thereof. For example, the modified base can be a propargylamino cytosine, a propargylamino uracil, a propargylamino thymine, a propargylamino adenine, or a propargylamino guanine. For example, the modified base can be a aminoallyl cytosine, a aminoallyl uracil, a aminoallyl thymine, a aminoallyl adenine, or a aminoallyl guanine. For example, the modified base can be a propargylhydroxyl cytosine, a propargylhydroxyl uracil, a propargylhydroxyl thymine, a propargylhydroxyl adenine, or a propargylhydroxyl guanine.

Photocleavable Carbon Chain

In some embodiments, the photocleavable carbon chain moiety comprises a saturated or unsaturated, substituted or unsubstituted, straight or branched carbon chain. The length of the photocleavable carbon chain can be different in different embodiments. In some embodiments, the photocleavable carbon chain has a length of, of about, of at least, of at least about, of at most, or of at most about, 10 Å, 11 Å, 12 Å, 13 Å, 14 Å, 15 Å, 16 Å, 17 Å, 18 Å, 19 Å, 20 Å, 21 Å, 22 Å, 23 Å, 24 Å, 25 Å, 26 Å, 27 Å, 28 Å, 29 Å, 30 Å, 31 Å, 32 Å, 33 Å, 34 Å, 35 Å, 36 Å, 37 Å, 38 Å, 39 Å, 40 Å, 41 Å, 42 Å, 43 Å, 44 Å, 45 Å, 46 Å, 47 Å, 48 Å, 49 Å, 50 Å, 51 Å, 52 Å, 53 Å, 54 Å, 55 Å, 56 Å, 57 Å, 58 Å, 59 Å, 60 Å, 61 Å, 62 Å, 63 Å, 64 Å, 65 Å, 66 Å, 67 Å, 68 Å, 69 Å, 70 Å, 71 Å, 72 Å, 73 Å, 74 Å, 75 Å, 76 Å, 77 Å, 78 Å, 79 Å, 80 Å, 81 Å, 82 Å, 83 Å, 84 Å, 85 Å, 86 Å, 87 Å, 88 Å, 89 Å, 90 Å, 91 Å, 92 Å, 93 Å, 94 Å, 95 Å, 96 Å, 97 Å, 98 Å, 99 Å, 100 Å, 200 Å, 300 Å, 400 Å, 500 Å, 600 Å, 700 Å, 800 Å, 900 Å, 1000 Å, or a number or a range between any two of these values. For example, the carbon chain has a length of at least 60 Å.

The photocleavable carbon chain moiety can comprise one or more carbon atoms, zero, one, or more oxygen atoms, zero, one or more nitrogen atoms, zero, one, or more sulfur atoms, or a combination thereof, in different embodiments. In some embodiments, the photocleavable carbon chain moiety comprises, comprises about, comprises at least, comprises at least about, comprises at most, or comprises at most about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values, carbon atom(s), oxygen atom(s), nitrogen atom(s), sulfur atom(s), or a combination thereof. For example, the photocleavable carbon chain moiety comprises at least 54 carbon, oxygen, nitrogen, and/or sulfur atoms. The photocleavable carbon chain moiety can comprise one or more carbon atoms, zero, one, or more oxygen atoms, zero, one or more nitrogen atoms, zero, one, or more sulfur atoms, or a combination thereof, in the main chain of the photocleavable carbon chain moiety in different embodiments. In some embodiments, the photocleavable carbon chain moiety comprises, comprises about, comprises at least, comprises at least about, comprises at most, or comprises at most about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values, carbon atom(s), oxygen atom(s), nitrogen atom(s), sulfur atom(s), or a combination thereof, in the main chain of the carbon chain moiety. For example, the photocleavable carbon chain moiety comprises at least 54 carbon, oxygen, nitrogen, and/or sulfur atoms in the main chain of the photocleavable carbon chain.

In some embodiments, the photocleavable carbon chain moiety comprises a polymer, such as a homopolymer or a heteropolymer. In some embodiments, the photocleavable carbon chain moiety comprises a plurality of repeat units. In some embodiments, the plurality of repeating units comprises identical repeating units. In some embodiments, the plurality of repeating units comprises two or more different repeating units. The plurality of repeating units can comprise a polyether such as paraformaldehyde, polyethylene glycol (PEG), polypropylene glycol (PPG), polyalkylene glycol (PAG), polytetramethylene glycol (PTMG), or a combination thereof. For example, the plurality of repeating units can comprise $PEG_{18}$, $PEG_{23}$, $PEG_{24}$, or a combination thereof. The plurality of repeating units can comprise a polyalkylene, such as polyethene, polypropene, polybutene, or a combination thereof. In some embodiments, a repeating unit of the plurality of repeating units comprises no aromatic group. In some embodiments, a repeating unit of the plurality of repeating units comprises one or more aromatic groups.

A repeating unit of the plurality repeating units can comprise one or more carbon atoms, zero, one, or more oxygen atoms, zero, one, or more nitrogen atoms, zero, one, or more sulfur atoms, or a combination thereof. For example, a repeating unit of the plurality of repeating units can comprise oxyethylene comprising two carbon atoms and one oxygen atom. In some embodiments, one or each of the plurality of repeating units comprises, comprises about, comprises at least, comprises at least about, comprises at most, or comprises at most about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, carbon atom(s), oxygen atom(s), nitrogen atom(s), sulfur atom(s), or a combination thereof. For example, one or each of the plurality repeating units comprises a saturated or unsaturated, substituted or unsubstituted, straight or branched carbon chain. For example, one or of the plurality of repeating units comprises a $C_1$ alkyl group, a C2 alkyl group, a C3 alkyl group, a C4 alkyl group, a $C_5$ alkyl group, or a C6 alkyl group, A repeating unit of the plurality repeating units can comprise one or more carbon atoms, zero, one, or more oxygen atoms, zero, one, or more nitrogen atoms, zero, one, or more sulfur atoms, or a combination thereof, in the main chain of the repeating unit. For example, a repeating unit of the plurality of repeating units can comprise oxyethylene comprising two carbon atoms and one oxygen atom in the main chain of the repeating unit. In some embodiments, one or each of the plurality of repeating units comprises, comprises about, comprises at least, comprises at least about, comprises at most, or comprises at most about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, carbon atom(s), oxygen atom(s), nitrogen atom(s), sulfur atom(s), or a combination thereof, in the main chain of the repeating unit. For example, one or each of the plurality of repeating units comprises a saturated or unsaturated, substituted or unsubstituted carbon chain in the main chain of the repeating unit. For example, one or each of the plurality of repeating units comprises a saturated or unsaturated, substituted or unsubstituted alkyl group in the main chain of the repeating unit. For example, one or each of the plurality of repeating units comprises a methyl group, an ethyl group, a propyl group, a butyl group, or a hexyl group in the main chain of the repeating unit. For example, one or each of the plurality of repeating units comprises a methoxy group, an ethoxy group, a propoxy group, a butoxy group, or a hexoy group in the main chain of the repeating unit.

The number of the plurality of repeating units can be different in different embodiments. In some embodiments, the number of the plurality of repeating units is, is about, is at least, is at least about, is at most, or is at most about, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values. For example, the number of the plurality of repeating units is at least 18, 23, or 24. For example, the plurality of repeating units can comprise $PEG_{18}$, $PEG_{23}$, $PEG_{24}$, or a combination thereof.

Photocleavable Moiety

In some embodiments, the photocleavable carbon chain moiety comprises a photocleavable moiety selected from a group consisting of a carbonyl group, an arylcarbonylmethyl group, a phenacyl group, an o-alkylphenacyl group, a p-hydroxyphenacyl group, a benzoin group, a benzyl group, a nitroaryl group, a nitrobenzyl group, an o-nitrobenzyl group, an o-nitro-2-phenethyloxycarbonyl group, an o-nitroanilide, a coumarin-4-ylmethyl group, an arylmethyl group, a coumaryl group, an o-hydroxyarylmethyl group, a metal-containing group, a pivaloyl group, an ester of a carboxylic acid, an arylsulfonyl group, a ketone group, a carbanion-mediated group, a sisyl group, a silicon-based group, a 2-hydroxycinnamyl group, an α-keto amide group, an α,β-unsaturated anilide, a methyl(phenyl)thiocarbamic acid group, a thiochromone S,S-dioxide group, 2-pyrrolidino-1,4-benzoquinone group, a triazine group, an arylmethyleneimino group, a xanthene group, a pyronin group, a 7-hydroxy-1,1-dimethylnaphthalenone group, a carboxylic acid group, a phosphate group, a phosphite group, a sulfate group, an acid group, an alcohol group, a thiol group, a N-oxide group, a phenol group, an amine group, a derivative of any of the proceeding, or a combination thereof.

TdT

The concentration of a TdT of the present disclosure (e.g., the first TdT and the second TdT) can be different in different embodiments. In some embodiments, the concentration of the TdT is, is about, is at least, is at least about, is at most, or is at most about, 0.1 nM, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, 1 μM, 2 μM, 3 μM, 4 μM, 5 μM, 6 μM, 7 μM, 8 μM, 9 μM, 10 μM, 20 μM, 30 μM, 40 μM, 50 μM, 60 μM, 70 μM, 80 μM, 90 μM, 100 μM, or a number or a range between any two of these values. For example, the concentration of the TdT is at least 10 nM.

In some embodiments, the TdT (e.g., the first TdT and the second TdT) comprises a recombinant TdT. In some embodiments, the first TdT and the second TdT are identical. In some embodiments, the first TdT and the second TdT comprise an identical molecule of a TdT. In some embodiments, the first TdT and the second TdT comprise different molecules of a TdT. An identical molecule of a TdT or different molecules of a TdT can be used for multiple incorporation reactions. For example, molecules of the TdT can be attached to one or more magnetic beads or particles. The TdT can be introduced into the $n^{th}$ incorporation reaction during the $n^{th}$ contacting step by introducing the magnetic beads or particles into the $n^{th}$ incorporation reaction. After the $n^{th}$ incorporation reaction or contacting step and before the $n^{th}$ photocleavage reaction or step, the method can comprise removing molecules of the TdT from the $n^{th}$ incorporation reaction by magnetically removing the magnetic beads or particles from the $n^{th}$ incorporation reaction. The TdT can be introduced into the $(n+1)^{th}$ incorporation reaction during the $(n+1)^{th}$ contacting step by introducing the same magnetic beads or particles used in the $n^{th}$ incorporation reaction or contacting step into the $(n+1)^{th}$ contacting reaction. In some embodiments, the first TdT and the second TdT comprise different TdTs.

Incorporation Reaction

An incorporation reaction or contacting step of the present disclosure (e.g., the $n^{th}$ incorporation reaction or contacting step in (b1), and the $(n+1)^{t}$ incorporation reaction or contacting step in (b2)) can occur or be performed at different incorporation reaction temperatures in different embodiments. In some embodiments, an incorporation reaction temperature is, is about, is at least, is at least about, is at most, or is at most about, 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., or a number or a range between any two of these values. For example, an incorporation reaction or contacting step is performed at about 16° C. to about 58° C.

The efficiency of an incorporation reaction or contacting step of the present disclosure (e.g., the e.g., the $n^{th}$ incorporation reaction or contacting step, or the $(n+1)^{th}$ incorporation reaction or contacting step) can be different in different embodiments. In some embodiments, the efficiency of an incorporation reaction or contacting step of the present disclosure is, is about, is at least, is at least about, is at most, or is at most about, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, 99.99%, 100%, or a number or a range between any two of these values. For example, the first modified nucleic acid in step (b1) comprises at least 95% of the nucleic acid to which the first nucleoside triphosphate is incorporated. As another example, the second modified nucleic acid in step (b2) comprises at least 95% of the first modified nucleic acid to which the second nucleoside triphosphate is incorporated. For example, at least 95% of the first modified nucleic acid in step (b1) comprises the first modified nucleic acid comprising the nucleic acid incorporated with a single first nucleotide from the first nucleoside triphosphate. At least 95% of the second modified nucleic acid in step (b2) can comprise the second modified nucleic acid comprising the first modified nucleic acid incorporated with a single second nucleotide from the second nucleoside triphosphate.

In some embodiments, the percentage of the modified nucleic acid generated after a plurality of iterations is, is about, is at least, is at least about, is at most, or is at most about, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, 99.99%, 100%, or a number or a range between any two of these values. For example, at least 95% of the modified nucleic acid generated after a plurality of iterations comprises the predetermined sequence.

Photocleavage Reaction

A photocleavage reaction or photocleaving step of the present disclosure (e.g., the $n^{th}$ photocleavage reaction or photocleaving in step (c1), and the $(n+1)^{th}$ photocleavage reaction or photocleaving in step (c2)) can be performed with a radiation. For example, the $n^{th}$ photocleavage reaction or the photocleaving in step (c1) is performed with a first radiation. The $(n+1)^{th}$ photocleavage reaction or photocleaving in step (c2) can be performed with a second radiation. The first radiation and the second radiation can be identical. The first radiation and the second radiation can be different. The radiation of a photocleavage reaction or photocleaving step can be different in different embodiments. In some embodiments, the radiation of a photocleavage reaction or photocleaving step has a wattage of, of about, of at least, of at least about, of at most, or of at most about, 1 watt, 2 watts, 3 watts, 4 watts, 5 watts, 6 watts, 7 watts, 8 watts, 9 watts, 10 watts, 11 watts, 12 watts, 13 watts, 14 watts, 15 watts, 16 watts, 17 watts, 18 watts, 19 watts, 20 watts, 21 watts, 22 watts, 23 watts, 24 watts, 25 watts, 26 watts, 27 watts, 28 watts, 29 watts, 30 watts, 31 watts, 32 watts, 33 watts, 34 watts, 35 watts, 36 watts, 37 watts, 38 watts, 39 watts, 40 watts, 41 watts, 42 watts, 43 watts, 44 watts, 45 watts, 46 watts, 47 watts, 48 watts, 49 watts, 50 watts, 51 watts, 52 watts, 53 watts, 54 watts, 55 watts, 56 watts, 57 watts, 58 watts, 59 watts, 60 watts, 61 watts, 62 watts, 63 watts, 64 watts, 65 watts, 66 watts, 67 watts, 68 watts, 69 watts, 70 watts, 71 watts, 72 watts, 73 watts, 74 watts, 75 watts, 76 watts, 77 watts, 78 watts, 79 watts, 80 watts, 81 watts, 82 watts, 83 watts, 84 watts, 85 watts, 86 watts, 87 watts, 88 watts, 89 watts, 90 watts, 91 watts, 92 watts, 93 watts, 94 watts, 95 watts, 96 watts, 97 watts, 98 watts, 99 watts, 100 watts, or a number or a range between any two of these values. For example, the first radiation used in the $n^{th}$ photocleavage reaction or photocleaving in step (c1) and the second radiation used in the $(n+1)^{th}$ photocleavage reaction or photocleaving in step (c2) have a wattage of about 5 watts to about 20 watts.

In some embodiments, a radiation used in a photocleavage reaction or photocleaving step comprises an ultraviolet (UV) radiation. The radiation can have different wavelengths in different embodiments. In some embodiments, the radiation has a wavelength of, of about, of at least, of at least about, of at most, or of at most about, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, or a number or a range between any two of these values. For example, the first radiation used in the $n^{th}$ photocleavage reaction or photocleaving in step (c1) and the second radiation used in the $(n+1)^{th}$ photocleavage reaction or photocleaving in step (c2) have a wavelength of about 300 nm to about 400 nm.

A radiation used in a photocleavage reaction or photocleaving step can be generated using a lamp, such as an ultraviolet (UV) lamp. The wattage of the lamp used to generate the radiation can be different in different embodiments. In some embodiments, the lamp used to generate the radiation has a wattage of, of about, of at least, of at least about, of at most, or of at most about, 1 watt, 2 watts, 3 watts, 4 watts, 5 watts, 6 watts, 7 watts, 8 watts, 9 watts, 10 watts, 11 watts, 12 watts, 13 watts, 14 watts, 15 watts, 16 watts, 17 watts, 18 watts, 19 watts, 20 watts, 21 watts, 22 watts, 23 watts, 24 watts, 25 watts, 26 watts, 27 watts, 28 watts, 29 watts, 30 watts, 31 watts, 32 watts, 33 watts, 34 watts, 35 watts, 36 watts, 37 watts, 38 watts, 39 watts, 40 watts, 41 watts, 42 watts, 43 watts, 44 watts, 45 watts, 46 watts, 47 watts, 48 watts, 49 watts, 50 watts, 51 watts, 52 watts, 53 watts, 54 watts, 55 watts, 56 watts, 57 watts, 58 watts, 59 watts, 60 watts, 61 watts, 62 watts, 63 watts, 64 watts, 65 watts, 66 watts, 67 watts, 68 watts, 69 watts, 70 watts, 71 watts, 72 watts, 73 watts, 74 watts, 75 watts, 76 watts, 77 watts, 78 watts, 79 watts, 80 watts, 81 watts, 82 watts, 83 watts, 84 watts, 85 watts, 86 watts, 87 watts, 88 watts, 89 watts, 90 watts, 91 watts, 92 watts, 93 watts, 94 watts, 95 watts, 96 watts, 97 watts, 98 watts, 99 watts, 100 watts, or a number or a range between any two of these values. For example, the first radiation used in the $n^{th}$ photocleavage reaction or photocleaving in step (c1) and the second radiation used in the $(n+1)^{th}$ photocleavage reaction or photocleaving in step (c2) are generated using a lamp with a wattage of about 10 watts to about 60 watts.

A photocleavage reaction or photocleaving step can have different photocleavage efficiencies in different embodiments. In some embodiments, a photocleavage reaction or photocleaving step has a photocleavage efficiency of, of about, of at least, of at least about, of at most, or of at most about, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, 99.99%, 100%, or a number or a range between any two of these values. For example, the $n^{th}$ photocleavage reaction or photocleaving in step (c1) and the $(n+1)^{th}$ photocleavage reaction or photocleaving in step (c2) each has a photocleavage efficiency of at least 90%.

A photocleavage reaction or photocleaving step of the present disclosure (e.g., the $n^{th}$ photocleavage reaction or photocleaving step in (x1), and the $(n+1)^{th}$ photocleavage reaction or photocleaving step in (c2)) can occur or be performed at different photocleavage reaction temperatures in different embodiments. In some embodiments, a photocleavage reaction temperature is, is about, is at least, is at least about, is at most, or is at most about, 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., or a number or a range between any two of these values. For example, the $n^{th}$ photocleavage reaction or photocleaving in step (c1) and the $(n+1)^{th}$ photocleavage reaction or photocleaving in step (c2) each is performed at about 16° C. to about 58° C.

Reaction Times

An incorporation reaction or contacting step of the present disclosure (e.g., the $n^{th}$ incorporation reaction or contacting step in (b1), and the $(n+1)^{th}$ incorporation reaction or contacting step in (b2)) can be performed for or completed in different incorporation reaction times in different embodiments. In some embodiments, an incorporation reaction time is, is about, is at least, is at least about, is at most, or is at most about, 1 min, 2 mins, 3 mins, 4 mins, 5 mins, 6 mins, 7 mins, 8 mins, 9 mins, 10 mins, 11 mins, 12 mins, 13 mins, 14 mins, 15 mins, 16 mins, 17 mins, 18 mins, 19 mins, 20 mins, 21 mins, 22 mins, 23 mins, 24 mins, 25 mins, 26 mins, 27 mins, 28 mins, 29 mins, 30 mins, or a number or a range between any two of these values. For example, an incorporation reaction or contacting step is performed for or completed in about 5 minutes to about 20 minutes. As another example, an incorporation reaction or contacting step is performed for or completed in about 7 minutes.

A photocleavage reaction or photocleaving step (e.g., the photocleaving in step (c1), and the photocleaving in step (c2)) can be performed for or completed in different photocleavage reaction times. In some embodiments, a photocleavage reaction time is, is about, is at least, is at least about, is at most, or is at most about, 1 sec, 2 secs, 3 secs, 4 secs, 5 secs, 6 secs, 7 secs, 8 secs, 9 secs, 10 secs, 11 secs, 12 secs, 13 secs, 14 secs, 15 secs, 16 secs, 17 secs, 18 secs, 19 secs, 20 secs, 21 secs, 22 secs, 23 secs, 24 secs, 25 secs, 26 secs, 27 secs, 28 secs, 29 secs, 30 secs, 31 secs, 32 secs, 33 secs, 34 secs, 35 secs, 36 secs, 37 secs, 38 secs, 39 secs, 40 secs, 41 secs, 42 secs, 43 secs, 44 secs, 45 secs, 46 secs, 47 secs, 48 secs, 49 secs, 50 secs, 51 secs, 52 secs, 53 secs, 54 secs, 55 secs, 56 secs, 57 secs, 58 secs, 59 secs, 1 min, 2 mins, 3 mins, 4 mins, 5 mins, 6 mins, 7 mins, 8 mins, 9 mins, 10 mins, 11 min, 12 mins, 13 mins, 14 mins, 15 mins, 16 mins, 17 mins, 18 mins, 19 mins, 20 mins, 21 min, 22 mins, 23 mins, 24 mins, 25 mins, 26 mins, 27 mins, 28 mins, 29 mins, 30 mins, or a number or a range between any two of these values. For example, a photocleavage reaction or photocleaving step is performed for or completed in about 1 minute. As another example, a photocleavage reaction or photocleaving step is performed for about 1 minute to about 20 minutes.

The total reaction time of an iteration of (b) an incorporation reaction or contacting step and (c) a photocleavage reaction or photocleaving step can be different in different embodiments. In some embodiments, the total reaction time of an iteration of (b) an incorporation reaction or contacting step and (c) a photocleavage reaction or photocleaving step is, is about, is at least, is at least about, is at most, or is at most about, 1 min, 2 mins, 3 mins, 4 mins, 5 mins, 6 mins, 7 mins, 8 mins, 9 mins, 10 mins, 11 mins, 12 mins, 13 mins, 14 mins, 15 mins, 16 mins, 17 mins, 18 mins, 19 mins, 20 mins, 21 mins, 22 mins, 23 mins, 24 mins, 25 mins, 26 mins, 27 mins, 28 mins, 29 mins, 30 mins, 31 mins, 32 mins, 33 mins, 34 mins, 35 mins, 36 mins, 37 mins, 38 mins, 39 mins, 40 mins, 41 min, 42 mins, 43 mins, 44 mins, 45 mins, 46 mins, 47 mins, 48 mins, 49 mins, 50 mins, 51 min, 52 mins, 53 mins, 54 mins, 55 mins, 56 mins, 57 mins, 58 mins, 59 mins, 60 mins or a number or a range between any two of these values. For example, the contacting in step (b1) and the photocleaving in step (c1) are completed in about 10 minutes. As another example, the contacting in step (b2) and the photocleaving in step (c2) are completed in about 10 minutes.

Reverse Complement

In some embodiments, the method comprises: generating a reverse complement of the modified nucleic acid using a polymerase. The reverse complement can be generated using the polymerase when the modified nucleic acid is attached to the solid support. The reverse complement can be generated using the polymerase after the modified nucleic acid is detached from the solid support.

Nucleoside Triphosphate

Disclosed herein include embodiments of a plurality of nucleoside triphosphates for nucleotide synthesis a terminal deoxynucleotidyl transferase (TdT). Each of the plurality of nucleotide triphosphate can comprise a modified base, the modified base comprises a photocleavable carbon chain moiety having a length of at least 30 Å.

In some embodiments, the photocleavable moiety is photocleavable by a radiation with a wattage of, of about, of at least, of at least about, of at most, or of at most about, 1 watt, 2 watts, 3 watts, 4 watts, 5 watts, 6 watts, 7 watts, 8 watts, 9 watts, 10 watts, 11 watts, 12 watts, 13 watts, 14 watts, 15 watts, 16 watts, 17 watts, 18 watts, 19 watts, 20 watts, 21 watts, 22 watts, 23 watts, 24 watts, 25 watts, 26 watts, 27 watts, 28 watts, 29 watts, 30 watts, 31 watts, 32 watts, 33 watts, 34 watts, 35 watts, 36 watts, 37 watts, 38 watts, 39 watts, 40 watts, 41 watts, 42 watts, 43 watts, 44 watts, 45 watts, 46 watts, 47 watts, 48 watts, 49 watts, 50 watts, 51 watts, 52 watts, 53 watts, 54 watts, 55 watts, 56 watts, 57 watts, 58 watts, 59 watts, 60 watts, 61 watts, 62 watts, 63 watts, 64 watts, 65 watts, 66 watts, 67 watts, 68 watts, 69 watts, 70 watts, 71 watts, 72 watts, 73 watts, 74 watts, 75 watts, 76 watts, 77 watts, 78 watts, 79 watts, 80 watts, 81 watts, 82 watts, 83 watts, 84 watts, 85 watts, 86 watts, 87 watts, 88 watts, 89 watts, 90 watts, 91 watts, 92 watts, 93 watts, 94 watts, 95 watts, 96 watts, 97 watts, 98 watts, 99 watts, 100 watts, or a number or a range between any two of these values.

In some embodiments, the photocleavable moiety is photocleavable by a radiation in, in about, in at least, in at least about, in at most, or in at most about, 1 sec, 2 secs, 3 secs, 4 secs, 5 secs, 6 secs, 7 secs, 8 secs, 9 secs, 10 secs, 11 secs, 12 secs, 13 secs, 14 secs, 15 secs, 16 secs, 17 secs, 18 secs, 19 secs, 20 secs, 21 secs, 22 secs, 23 secs, 24 secs, 25 secs, 26 secs, 27 secs, 28 secs, 29 secs, 30 secs, 31 secs, 32 secs, 33 secs, 34 secs, 35 secs, 36 secs, 37 secs, 38 secs, 39 secs, 40 secs, 41 secs, 42 secs, 43 secs, 44 secs, 45 secs, 46 secs, 47 secs, 48 secs, 49 secs, 50 secs, 51 secs, 52 secs, 53 secs, 54 secs, 55 secs, 56 secs, 57 secs, 58 secs, 59 secs, 1 min, 2 mins, 3 mins, 4 mins, 5 mins, 6 mins, 7 mins, 8 mins, 9 mins, 10 mins, 11 min, 12 mins, 13 mins, 14 mins, 15 mins, 16 mins, 17 mins, 18 mins, 19 mins, 20 mins, 21 min, 22 mins, 23 mins, 24 mins, 25 mins, 26 mins, 27 mins, 28 mins, 29 mins, 30 mins, or a number or a range between any two of these values.

In some embodiments, the photocleavable moiety is photocleavable by a radiation at a temperature of, of about, of at least, of at least about, of at most, or of at most about, 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., or a number or a range between any two of these values.

In some embodiments, the photocleavable moiety is photocleavable by a radiation with an efficiency of, of about, of at least, of at least about, of at most, or of at most about, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, 99.99%, 100%, or a number or a range between any two of these values.

In some embodiments, the photocleavable moiety is photocleavable by a radiation with a wavelength of, of about, of at least, of at least about, of at most, or of at most about, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, or a number or a range between any two of these values.

For example, the photocleavable moiety is photocleavable by a radiation with a wattage of about 5 watts to about 20 watts in about 1 minute to about 20 minutes at about 16° C. to about 58° C. with an efficiency of at least 90%. In some embodiments, the radiation comprises an ultraviolet (UV) radiation. In some embodiments, the radiation has a wavelength of about 300 nm to about 400 nm.

EXAMPLE

Some aspects of the embodiments discussed above are disclosed in further detail in the following example, which is not in any way intended to limit the scope of the present disclosure.

Example 1

Base-Modified Nucleotides as Substrates for TdT-Based Enzymatic Nucleic Acid Synthesis Deoxyribonucleic acid (DNA) can be synthesized using a four-step chemical method based on phosphoramidite chemistry, allowing synthesis of DNA strands up to 250-300 base pairs. Enzymatic gene synthesis is an alternative to achieve the synthesis of DNA sequences, such as long DNA sequences. The Terminal Deoxynucleotidyl Transferase (TdT) is a template-independent DNA polymerase that can be used for such enzymatic based gene synthesis. In order to achieve incorporation of a single nucleotide at a time with TdT, a reversible blocking group can be present either at the 3' hydroxyl position of the nucleotide or at the nucleobase. This example describes a systematic study on the size of the nucleobase blocking group to allow for a single incorporation event, while keeping the 3' hydroxyl position of the nucleotide unprotected. Various lengths of polyethylene glycol (PEG) were conjugated to the C5-position of pyrimidines and the C7-position of 7-deazapurines of nucleotides. The formation of the desired +1 product was observed in a quantitative yield with a PEG24 block at the nucleobase. The formation of the desired +1 product was demonstrated with all four PEG-modified nucleotides. PEG-modified nucleotides can be used for enzymatic DNA synthesis, and the size of the PEG modification can be adjusted to prevent more than one incorporation event.

Introduction

Traditionally, DNA has been synthesized using a four-step chemical method based on phosphoramidite chemistry. By controlling depurination, the synthesis of oligonucleotides 250-300 nucleotides in length can be achieved. There is a need for the synthesis of longer DNA fragments in the fields of synthetic biology and biotechnology. The ability to synthesize genes can be important in the synthesis of whole bacterial and yeast genomes, and enables the discovery of novel proteins. In addition, studies have shown that DNA can be an excellent candidate for data storage due to its higher 3-dimensional density and stability for long term storage. These developments have driven the demand for the synthesis of longer DNA oligonucleotides. Enzymatic DNA synthesis, using the Terminal deoxynucleotidyl Transferase (TdT) enzyme, is a promising method to synthesize longer DNA at lower cost (e.g., half the cost) of the phosphoramidite method.

The TdT enzyme, also known as the misguided polymerase, is a unique polymerase as TdT does not require a template strand for oligonucleotide synthesis. Since TdT can incorporate nucleotides indiscriminately, TdT can be used to achieve enzymatic gene synthesis. However, TdT incorporates more than 8000 bases over 24 hours when unmodified nucleotides are used. For TdT to be useful in enzymatic gene synthesis, TdT can perform a single incorporation every time a specific nucleotide is introduced. Such single incorporation allows the exact sequence of the DNA oligonucleotide desired to be synthesized. If multiple incorporations occur every time a specific nucleotide is introduced, there will not be control in the sequence synthesized.

There are two possible strategies to achieve controlled single incorporation events with TdT. The 3' hydroxyl (3'-OH) group of the nucleotide can be modified with a reversible blocking group, or the nucleobase can be modified with a reversible blocking group that prevents more than one incorporation. These reversible blocks can then be removed after the incorporation event, to allow the next incorporation to occur. Nucleotides with 3'-OH reversibly terminated have been studied extensively, especially in groups developing sequencing-by-synthesis methods. Illumina, Inc. (San Diego, California) developed the 3'-O-azidomethyl 2'-deoxynucleoside triphosphates as reversible terminators for sequencing. A palladium-based cleavable allyl reversible terminator for sequencing has been developed. The aminooxy blocking group as a reversible terminator for sequencing has been developed.

However, the use of 3' hydroxyl blocking groups on the nucleotides requires engineering of the natural TdT polymerase to accommodate the larger 3' block in the enzyme active site. Modification of human TdT at the nucleotide binding domain may result in significant loss of activity and stability. Only 3-16% of TdT's activity was retained when residues near the nucleotide binding side were mutated. TdT was evolved in an attempt to incorporate 3'-blocked nucleotides.

Use of Nucleobase Modification for TdT Incorporation

The second strategy to achieve single incorporation events is to have the blocking group at the nucleobase, while keeping the 3' hydroxyl position unblocked. Modifications at the 3' hydroxyl group directly impact the enzyme active site. However, modifications at the C5-position of pyrimidines or the C7-position of 7-deazapurines of nucleotides extend away from the enzyme active site and are more tolerated by polymerases. The development of the nucleobase modification that can block subsequent incorporations involves nucleotide engineering to optimize the size and attributes such as lipophilicity of the blocking group. In addition, the modified nucleotide can be efficiently incorporated by TdT, as well as block subsequent incorporations after its incorporation.

A few exemplary ways to achieve single incorporation events are described below. For example, dinucleotides have been used as virtual terminators for sequencing. The nucleotide design included a 3'-OH unblocked nucleotide, with a second inhibitor nucleotide introduced as a base modification via a disulfide linker. The disulfide linker was then cleaved using reducing reagents such as tris(2-carboxyethyl) phosphine. Another way to achieve single incorporation events is to attach a di-aspartate moiety as a nucleobase blocking group via a disulfide linker to achieve single incorporation events. Upon cleavage of the blocking group, the natural nucleobase was obtained, leaving no molecular scar. As another example, a TdT mutant enzyme has been conjugated to nucleotides with the TdT enzyme as a blocking group for further incorporations. The TdT enzyme included cysteines mutated to alanine or serine, and a single residue near the active site mutated to cysteine. These mutations enabled conjugation of maleimide functionalized nucleotides to the TdT enzyme. Higher incorporation rates were observed with the TdT-conjugated nucleotides compared to the unconjugated nucleotides. After incorporation, UV light at 365 nm was used to cleave the photocleavable linker. The cleaving step removed the TdT enzyme block from the growing oligonucleotide chain and a subsequent incorporation event can occur.

Modified nucleotides with $N^4$-aminocytosine, 4-thiouracil, 2-pyridone, 4-chloro- and 4-bromo-2-pyridone has been used as the nucleobase for TdT incorporation. Modifications on the 3' end of the growing oligonucleotide primer strand were hypothesized to enhance TdT-primer affinity. The enhanced TdT-primer affinity could play a role in blocking further incorporations of the incoming nucleotide. A structural study of the TdT-primer interaction had previously shown that interaction of the last three nucleobases on the primer oligonucleotide with TdT is required during extension. The incorporation of benzo-expanded nucleotides using TdT enzyme has been reported. TdT has been shown to incorporate 7-[2-(phenylsulfanyl)ethyl]-2'-deoxy-7-deazaadenosine 5'-O-triphosphate and 7-[2-(butylsulfanyl) ethyl]-2'-deoxy-7-deazaadenosine 5'-O-triphosphate, and only a single incorporation event was observed.

The example is a systematic study of the size requirement of the base-blocking group on nucleotides to achieve a single incorporation with TdT. Nucleotides were conjugated with varying lengths of polyethylene glycol (PEG) polymers at the nucleobase to determine the size requirement for blocking further incorporation events. The 3' hydroxyl position of the nucleotides were kept unblocked to reduce impact in the enzyme active site. The water-soluble PEG polymer chain was used as the blocking group for a systematic study as their lengths are highly tunable. The PEG groups were attached to the nucleobase via a photocleavable nitrobenzyl linker. The photocleavable nitrobenzyl linker allowed removal of the PEG blocking group to enable subsequent nucleotide incorporations by the TdT enzyme.

Material and Methods $^1$H NMR spectra (400 MHz or 500 MHz) were recorded on a JEOL ECA 400, Bruker Avance III 400 or Bruker Avance 500 spectrometer in various solvents [using TMS (for $^1$H, δ=0.00), MeOD (for $^1$H, δ=3.31) or $D_2O$ (for $^1$H, δ=4.79) as internal standard]. $^{13}$C NMR spectra (100 MHz) were recorded on a JEOL ECA 400 spectrometer in various solvents [using $CDCl_3$ (for $^{13}$C, δ=77.16), MeOD (for $^{13}$C, δ=49.00) as internal standard. $^{31}$P NMR spectra (160 MHz or 202 MHz) were recorded on a JEOL ECA 400 or Bruker Avance 500 spectrometer. The following abbreviations were used to explain the multiplicities: s=singlet, d=doublet, t=triplet, q=quartet, br=broad. High-resolution mass spectra were obtained with a Waters Q-Tof Premier mass spectrometer. Chemicals were purchased from Trilink Biotechnology (San Diego, California), Merck Group (Darmstadt, Germany), and Broadpharm (San Diego, California). Anhydrous solvents were purchased from Sigma-Aldrich (St. Louis, Missouri) and Acros Organics (Fair Lawn, New Jersey). TdT was purchased from New England Biolab (Ipswich, MA). TBE-Urea Gel (15%) was purchased from Life Technologies. All primers were synthesized by Integrated DNA Technologies (Coralville, Iowa). UV irradiation was done at a distance of less than 1 cm between lamp and sample using UVP 3 UV 8 W lamp at 365 nm.

Purification was performed on a Phenomenex (Torrance, California) Kinetex semi-preparative column (10×250 mm, 5 μm) using triethylammonium acetate (5 mM, pH 7.2) and acetonitrile as eluent on Shimadzu (Kyoto, Japan) Prominence HPLC. Anion exchange chromatography was performed on a Thermo Scientific (Waltham, Massachusetts) DNAPac PA-200 (9×250 mm, 8 μm) column using Tris (10 mM, pH 8) and NaCl (1 M) as eluent. Analysis of nucleotides was done using a Kinetex Evo C18 analytical column (3.0×50 mm, 2.6 μm) on an Agilent 1260 HPLC, monitoring at 260 nm, using TEAA (50 mM, pH 7.2) and acetonitrile as eluent.

DNA oligonucleotide sequence used for primer extension assays is: ATT CAG GAC GAG CCT CAG ACC (SEQ ID NO: 1)

General Method for Synthesis of $N_3$-$PEG_x$-dUTP (1-4)

$N_3$-$PEG_x$-N-hydroxysuccinimide ester ($N_3$-$PEG_x$-NHS ester, 4 equivalents) was dissolved in DMF (20 μL) and added to 5-propargylamino-deoxyuridine (8 μmol, 10 mM). The reaction was then stirred at room temperature for 16 hours under the dark environment. The reaction mixture was then purified by a semi-preparative anion exchange column (1% to 10% NaCl), evaporated under reduced pressure and further purified on a Kinetex Evo C18 semi-preparative column (0% to 50% ACN). The resulting residue was then freeze-dried to give the final product (FIG. 1A) as a triethylammonium salt.

$N_3$-$PEG_4$-dUTP (1)

Yield: 95 nmol, 44%. Electrospray ionization high-resolution mass spectrometry (ESI-HRMS) Found: m/z 793.1241; Calculated for $C_{23}H_{36}N_6O_{19}P_3$: (M-H)⁻ 793.1248.

$N_3$-$PEG_8$-dUTP (2)

Yield: 70 nmol, 35%. ESI-HRMS Found: m/z 969.2270; Calculated for $C_{31}H_{52}N_6O_{23}P_3$: (M-H)⁻ 969.2297.

$N_3$-$PEG_{12}$-dUTP (3)

Yield: 65 nmol, 33%. ESI-HRMS Found: m/z 1145.3335; Calculated for $C_{39}H_{68}N_9O_{27}P_3$: (M-H)⁻ 1145.3345.

$N_3$-$PEG_{24}$-dUTP (4)

Yield: 44 nmol, 22%. ESI-HRMS Found: m/z 1673.6444; Calculated for $C_{63}H_{116}N_6O_{39}P_3$: (M-H)⁻ 1673.6491.

$N_3$-$PEG_{23}$-nitrobenzyl (NB)-alcohol (5b)

To an ice cold solution of $N_3$-$PEG_{23}$-$NH_2$ (202 mg, 184 μmol, 1.1 equivalents) and 4-[4-(1-hydroxyethyl)-2-methoxy-5-nitrophenoxy]butyric acid (50 mg, 167 μmol, 1 equivalent) in tetrahydrofuran (THF, 2 mL) in a 4 mL vial containing a magnetic stir bar were added N,N'-dicyclohexylcarbodiimide (138 mg, 669 μmol, 4 equivalents) and hydroxybenzotriazole hydrate (68 mg, 442 μmol, 2.6 equivalents). The reaction mixture was stirred at the same temperature for 5 minutes before adding triethylamine (116 μL, 835 μmol, 5 equivalents). The reaction was then warmed up to room temperature and allowed to stir under the dark for 16 hours. The reaction mixture was then evaporated and the residue was dissolved in acetonitrile. The resulting solid materials were filtered off and purified by a semi-preparative Kinetex Evo C18 column to obtain yellow solid as the final product (170 mg, 123 μmol, 74%).

¹H NMR (396 MHz, $D_2O$) δ 7.55 (s, 1H), 7.35 (s, 1H), 5.44 (q, J=6.3 Hz, 1H), 4.09 (t, J=6.3 Hz, 2H), 4.00 (s, 3H), 3.77-3.58 (m, 92H), 3.51 (t, J=5.2 Hz, 2H), 3.41 (t, J=5.2 Hz, 2H), 2.46 (t, J=7.3 Hz, 2H), 2.21-2.06 (m, 2H), 1.47 (d, J=6.3 Hz, 3H).

¹³C NMR (100 MHz, $D_2O$) δ 175.28, 153.61, 146.31, 139.07, 137.49, 108.87, 108.67, 69.74, 69.59, 69.42, 69.01, 68.48, 65.17, 59.43, 56.30, 50.29, 39.10, 32.27, 24.85, 23.98.

ESI-HRMS Found: m/z 1424.7485; Calculated for $C_{62}H_{114}N_5O_{31}$: (M+FA-H)⁻ 1424.7498.

$N_3$-$PEG_{23}$-nitrobenzyl-dNTP (5-8)

To a solution of $N_3$-$PEG_{23}$-nitrobenzyl(NB)-alcohol (5b) in acetonitrile (2 mL) were added N,N'-disuccinimidyl carbonate and 4-dimethylaminopyridine, and the mixture was stirred for 4 hours at 40° C. The reaction was then diluted with water and the organic materials were extracted with dichloromethane. The aqueous layer was further extracted twice with dichloromethane. The combined organic layer was then washed with saturated $NaHCO_3$, 1M aq. HCl, brine, and dried over $Na_2SO_4$. The solvent was then removed under reduced pressure, and the resulting crude material containing $N_3$-$PEG_{23}$-NB—NHS ester (compound 5c) was used for the nest step without any further purification.

Figure 1B:
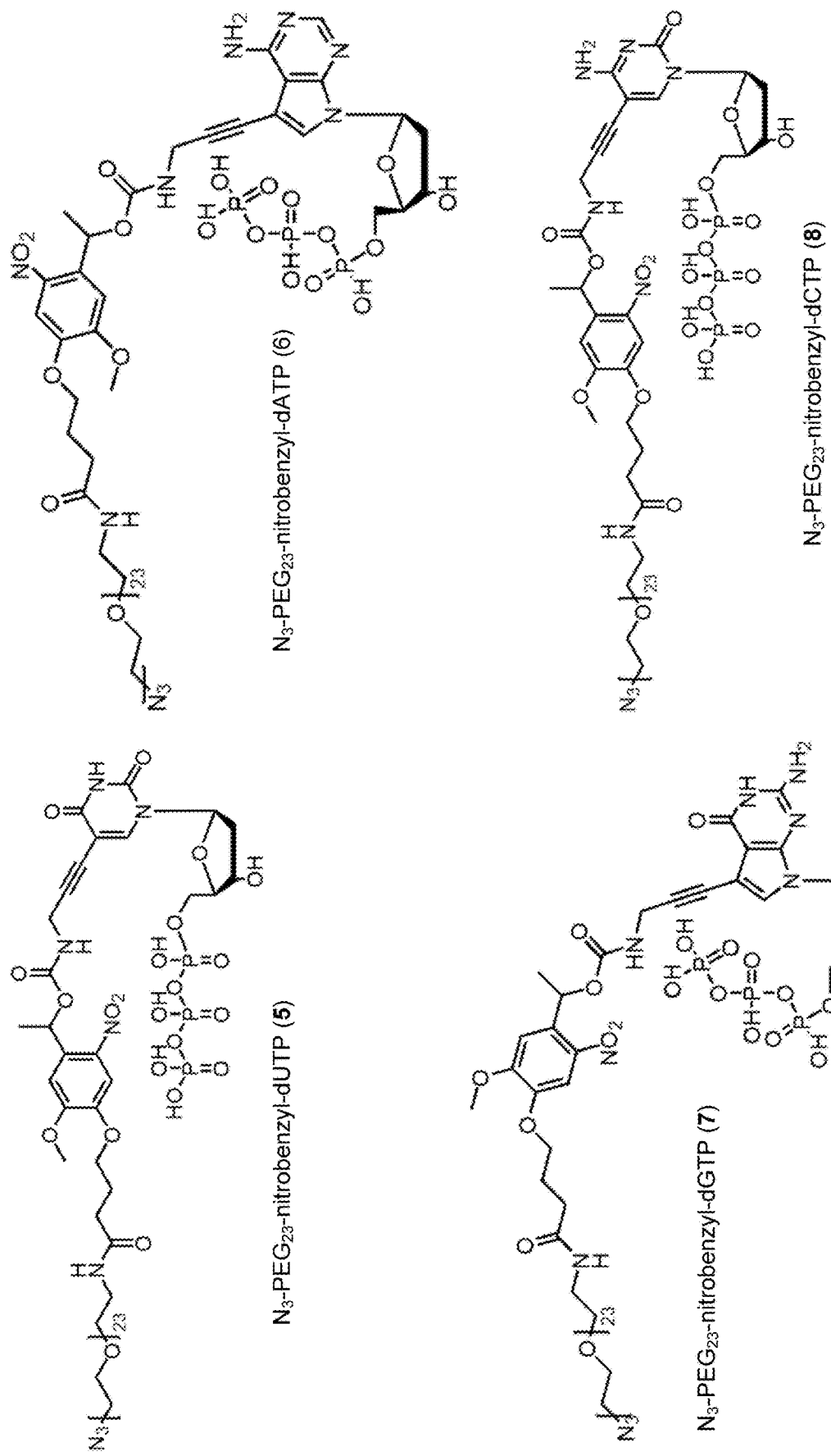
FIG. 1B. Structures of nucleotides 5-8.

The crude material containing compound 5c (2 equivalents) was dissolved in dimethylformamide (DMF, 20 μL) and 5-propargylamino-dNTP (8 μmol, 10 mM) was added to the mixture. The reaction was then stirred at room temperature for 16 hours under the dark. The reaction was then purified on a Kinetex Evo C18 semi-preparative column (0% to 50% ACN). The obtained residue was then freeze-dried to give the final product (FIG. 1B) as a triethylammonium salt.

$N_3$-$PEG_{23}$-nitrobenzyl-dUTP (5)

Yield: 0.72 μmol, 7%.

¹H NMR (400 MHz, $D_2O$) δ 8.08-7.92 (m, 1H), 7.55 (s, 1H), 7.11 (s, 1H), 6.28-5.96 (m, 2H), 4.15-3.65 (m, 9H), 3.63-3.41 (m, 96H), 3.39-3.36 (m, 2H), 3.28-3.22 (m, 2H), 2.89 (d, J=7.3 Hz, 3H), 2.36-2.18 (m, 4H), 2.07-1.91 (m, 2H), 1.51 (d, J=5.1 Hz, 3H).

³¹P NMR (162 MHz, $D_2O$) δ −10.26 (d, J=20 Hz), −11.03 (d, J=20 Hz), −22.72 (t, J=20 Hz).

ESI-HRMS Found: m/z 1925.7234; Calculated for $C_{74}H_{128}N_8O_{44}P_3$: (M-H)⁻ 1925.7237.

$N_3$-$PEG_{23}$-nitrobenzyl-dATP (6)

Yield: 0.81 μmol, 8%.

¹H NMR (400 MHz, $D_2O$) δ 8.22 (s, 1H), 7.75 (d, J=10.5 Hz, 1H), 7.52 (d, J=33.7 Hz, 1H), 7.11 (d, J=14.2 Hz, 1H), 6.58 (t, J=6.7 Hz, 1H), 6.20 (s, 1H), 4.23 (s, 3H), 4.14-4.01 (m, 1H), 3.80 (s, 3H), 3.72-3.62 (m, 95H), 3.59 (s, 4H), 3.52-3.48 (m, 2H), 3.42-3.34 (m, 2H), 2.67-2.43 (m, 2H), 2.43-2.32 (m, 2H), 1.59 (t, J=6.3 Hz, 3H).

³¹P NMR (121 MHz, $D_2O$) δ −10.10 (d, J=17.0 Hz), −10.70 (d, J=17.0 Hz), −22.40 (t, J=17.0 Hz).

ESI-HRMS Found: m/z 973.3661; Calculated for $C_{76}H_{129}N_{10}O_{42}P_3$: (M/2-H)⁻ 973.3740.

$N_3$-$PEG_{23}$-nitrobenzyl-dGTP (7)

Yield: 1.42 μmol, 14%.

¹H NMR (500 MHz, $D_2O$) δ 7.57 (s, 1H), 7.19 (d, J=28.3 Hz, 2H), 6.30 (t, J=7.0 Hz, 1H), 6.19 (s, 1H), 4.14 (s, 1H), 4.09 (d, J=5.7 Hz, 2H), 4.00 (s, 3H), 3.89 (s, 2H), 3.69-3.55 (m, 90H), 3.53 (s, 4H), 3.51 (t, J=5.2 Hz, 2H), 3.47-3.44 (m, 2H), 3.32 (t, J=5.4 Hz, 2H), 2.63-2.48 (m, 1H), 2.37 (t, J=7.1 Hz, 3H), 2.07-2.00 (m, 2H), 1.57 (s, 3H).

³¹P NMR (202 MHz, $D_2O$) δ −10.92 (d, J=19.9 Hz), −11.47 (d, J=19.9 Hz), −23.29 (t, J=19.9 Hz).

ESI-HRMS Found: m/z 981.3596; Calculated for $C_{76}H_{131}N_{10}O_{43}P_3$: (M/2-H)⁻ 981.3714.

$N_3$-$PEG_{23}$-nitrobenzyl-dCTP (8)

Yield: 0.95 μmol, 10%.

¹H NMR (396 MHz, $D_2O$) δ 8.11 (d, J=18.3 Hz, 1H), 7.63 (d, J=5.2 Hz, 1H), 7.18 (s, 1H), 6.25 (s, 1H), 6.16 (s, 1H), 4.19 (d, J=11.2 Hz, 3H), 4.06 (s, 3H), 3.93 (s, 3H), 3.70-3.61 (m, 90H), 3.56 (s, 5H), 3.48 (d, J=4.9 Hz, 2H), 2.41 (t, J=7.1 Hz, 3H), 2.09-2.03 (m, 3H), 1.61 (d, J=5.9 Hz, 3H).

³¹P NMR (160 MHz, $D_2O$) δ −10.34 (d, J=20.6 Hz), −11.00 (dt, J=20.6, 19.0 Hz), −22.80 (t, J=19.0 Hz).

ESI-HRMS Found: m/z 961.8527; Calculated for $C_{74}H_{128}N_9O_{43}P_3$: (M/2-H)⁻ 961.8660.

Screening of TdT Incorporation Conditions

A 6-fluorescein-tagged 21-nt oligonucleotide (200 nM), 1× TdT buffer (NEB), TdT (2 U μL⁻¹), $CoCl_2$ (NEB, 0.25 mM) and nucleotide (various concentration) in 20 solution were incubated at 37° C. for the specified time and quenched with an equal volume of Tris/Borate/EDTA (TBE)-Urea Gel loading dye (1×). The solution was then heated at 95° C. for 5 minutes to inactivate TdT. UV cleavage of the photolabile group was done using an 8 W UV lamp at 365 nm for 10 minutes.

2 Cycle Incorporation and Deprotection

A 6-fluorescein-tagged 21-nt oligonucleotide (200 nM), 1× TdT buffer (NEB), TdT (2 U μL⁻¹) $CoCl_2$ (NEB, 0.25 mM) and nucleotide (20 μM) in 500 μL solution was incubated at 37° C. for 7 minutes and quenched with EDTA (50 μL, 500 mM). The solution was concentrated using MilliporeSigma (Burlington, Massachusetts) Amicon Ultra-0.5 mL Centrifugal Filters (3 kDa) to a final volume of 30 μL. Sodium Acetate solution (10 μL, 3M, pH 5.0) was added to the concentrated solution and further purified using Zymo (Irvine, California) DNA Clean & Concentrator. UV cleavage of the photolabile group was done using an 8 W UV lamp at 365 nm for 10 minutes. The steps were then repeated to give the second incorporation.

Denaturing PAGE Gel

Initrogen (Carlsbad, California) Novex™ TBE-Urea gel (15%) was pre-washed with 1×TBE running buffer to remove excess urea. Oligonucleotide samples (5 µL) were mixed with Novex™ TBE-Urea Sample Buffer (2×, 5 µL). The mixture was then heated at 95° C. for 5 minutes and loaded to the gel. Gels were run in a 1×TBE running buffer at up to 240 V until the bromophenol blue reached the bottom of the gel. The gel was then visualized using Gel Doc XR+ and analyzed using the gel analysis tool in the Bio-Rad (Hercules, California) Image Lab software.

Results and Discussion

To study the effect of PEG chain lengths on the TdT incorporation, various lengths of PEGs, from four to twenty-four repeating units of ethylene glycol, were conjugated to propargylamino-dUTP. Azido-PEG$_x$-NHS ester (x=4, 8, 12, 24) was reacted with propargylamino-dUTP to give azido-PEG$_x$-dUTP (where x=4, 8, 12, 24) (FIG. 1). The yields of the reaction varied from 22% to 48.

Figure 2A:
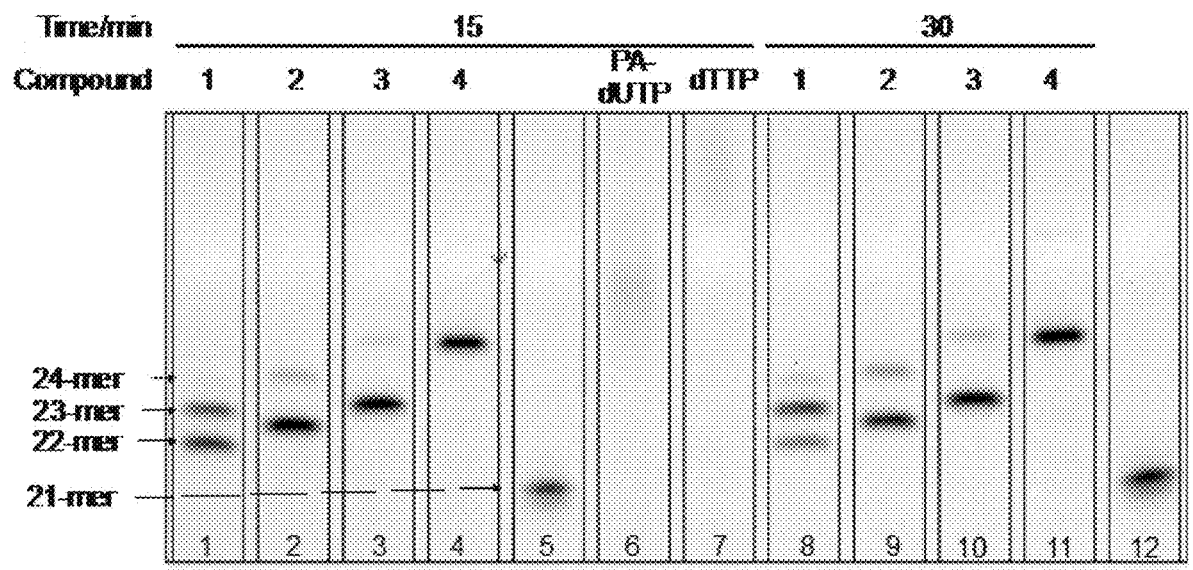
FIG. 2A. Denaturing TBE-Urea Gel showing incorporation of compounds 1-4 by TdT.
Figure 2B:
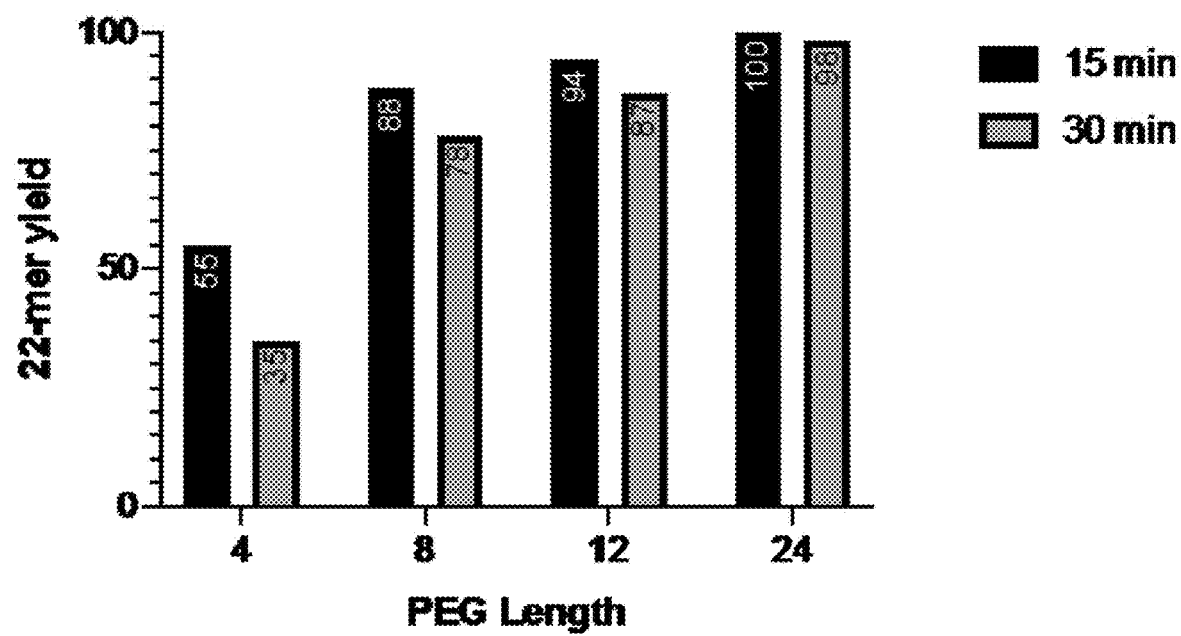
FIG. 2B. Bar graph showing effect of PEG length on 22-nt oligo yield.

Compounds 1~4 were then used for incorporation assays with TdT enzyme (FIGS. 2A-2B). Using 40 µM of nucleotide, 200 nM of 21-nt oligonucleotide for extension as well as 1 U µL$^{-1}$ of TdT, we observed various yield of 22-nt oligo (+1 product). When the shorter compound 1 (PEG$_4$) was used, the 22-nt (+1 product) was formed in 55% yield, together with a significant amount of 23-nt (+2 product) in 41% yield and some 24-nt oligo (+3 product) in 4% yield after 15 minutes (lane 1). Incorporation with Compound 2, with a PEG$_8$ base blocking group gave a much higher yield of the +1 product (88% yield) compared to the shorter PEG$_4$ modification (lane 2). Moreover, the yield of +2 product was significantly lower (12% yield) and +3 product was not observed. Further increase in PEG length to 12 repeating units (compound 3) shows better selectivity of +1 product in 94% (lane 3) and doubling the PEG length to 24 repeating units (compound 4) gave the desired 22-nt oligo (+1 product) in quantitative yield (lane 4). In addition, the incorporation of propargylamino-dUTP was significantly slower compared to that of dTTP (Lanes 6-7, FIG. 2A). Without being bound by any particular theory, the presence of a hydrophobic molecular scar might slow the activity of TdT. After incubating the mixtures for 30 minutes, the increase in yield of undesired 23-nt oligo increased (+2 product). Compound 1 gave lower 22-nt oligo (+1 product, 35%) while increasing the yield of undesired 23-nt (+2 product, 56%) and 24-nt (+3 product, 9%) oligo. Presence of 24-nt oligo (+3 product) was not observed for compound 2, 3 and 4. However, the increase in yield of 23-nt oligo was observed in compound 2 (+2 product, 22%) and compound 3 (+2 product, 13%) compared to the yield obtained with 15 minutes of incubation. In compound 4, only a small amount of 23-nt oligo (+2 product) was observed (2%).

A longer PEG chain as a base block gave a higher yield of the 22-nt oligo (+1 product), or a single incorporation event. While PEG$_4$ gave a yield of 55%, PEG$_{24}$ performed a quantitative incorporation after 15 minutes of incubation. After 30 minutes of incubation, a similar trend was observed where PEG$_4$ gave a yield of 35% compared to 98% yield when PEG$_{24}$ was used. These results show that the length of PEG can be tuned to achieve the incorporation efficiency.

FIG. 2A. Denaturing TBE-Urea Gel showing incorporation of compounds 1-4. Lane 1-4: Incorporation of compounds 1-4 (40 µM) respectively for 15 minutes. Lane 5 and 12: 21-nt oligonucleotide. Lane 6: Incorporation of propargylamino-dUTP (20 Lane 7: Incorporation of dTTP (20 Lanes 8-11: Incorporation of compounds 1~4 (40 µM) respectively for 30 minutes. FIG. 2B. Bar graph showing effect of PEG length on 22-nt oligo yield.

With these results, the PEG$_{23}$ moiety was attached to dNTPs through a photocleavable linker (Scheme 1). Amide bond formation was first carried out between amino-functionalized PEG$_{23}$ and 4-[4-(1-Hydroxyethyl)-2-methoxy-5-nitrophenoxy]butyric acid, giving compound 5b in 77% yield. To conjugate the photocleavable PEG with propargylamino-dUTP, 5b was then treated with N,N'-disuccinimidyl carbonate and the resulting carbonate 5c were further coupled with propargylamino-dUTP, affording the final product 5 in 7.2% yield.

Figure 3:
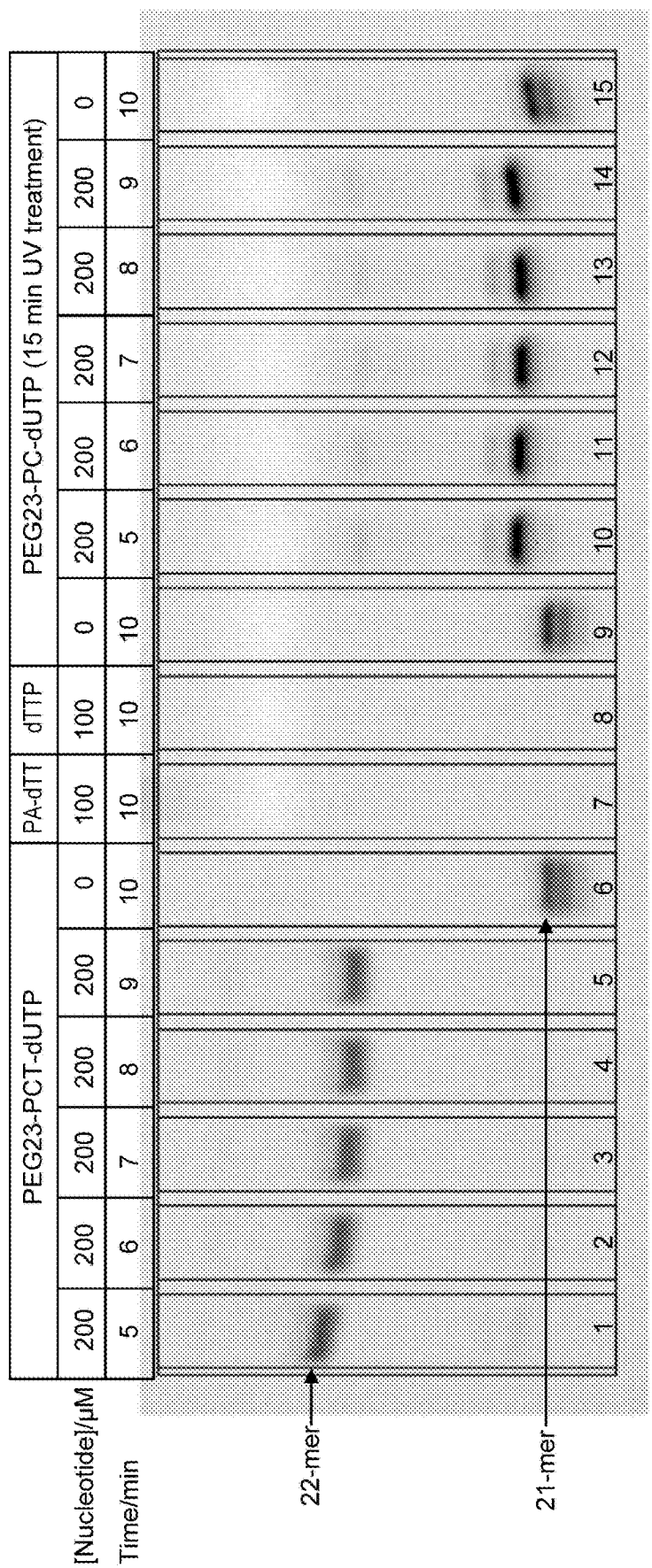
FIG. 3. Single, selective incorporation of compound 5 by TdT observed at 7 minutes of incubation with increasing incorporation time from 5 to 9 minutes.

The purified photocleavable PEG$_{23}$-dUTP 5 was then used for incorporation by TdT. The optimization of the reaction conditions revealed that quantitative incorporation was achieved within 7 minutes of the reaction time with compound 5 (FIG. 3). FIG. 3. Single, selective incorporation of compound 5 observed at 7 minutes of incubation with increasing incorporation time from 5 to 9 minutes in Lanes 1 to 5. Lanes 10 to 14 show +1 incorporation after photocleavage of PEG$_{23}$ nucleotide blocking group.

Scheme 1. Synthesis of Compound 5.

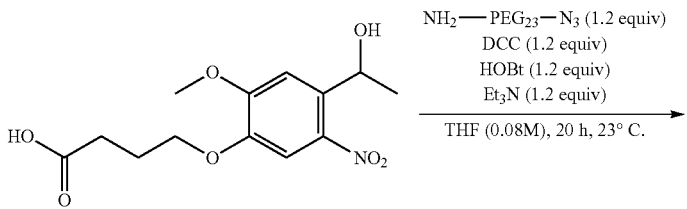

5a

NH$_2$—PEG$_{23}$—N$_3$ (1.2 equiv)
DCC (1.2 equiv)
HOBt (1.2 equiv)
Et$_3$N (1.2 equiv)
—————————————→
THF (0.08M), 20 h, 23° C.

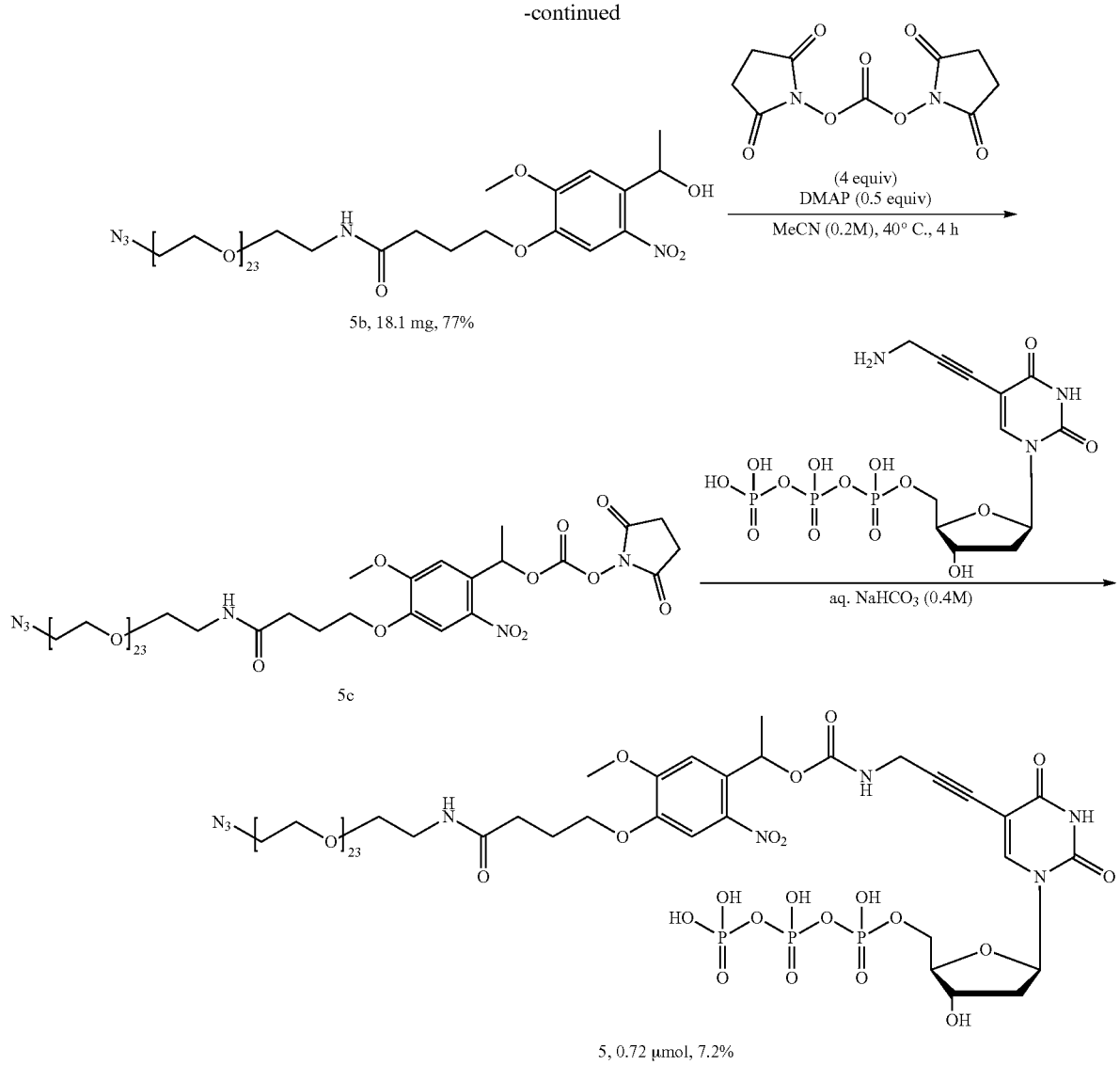

Figure 4:
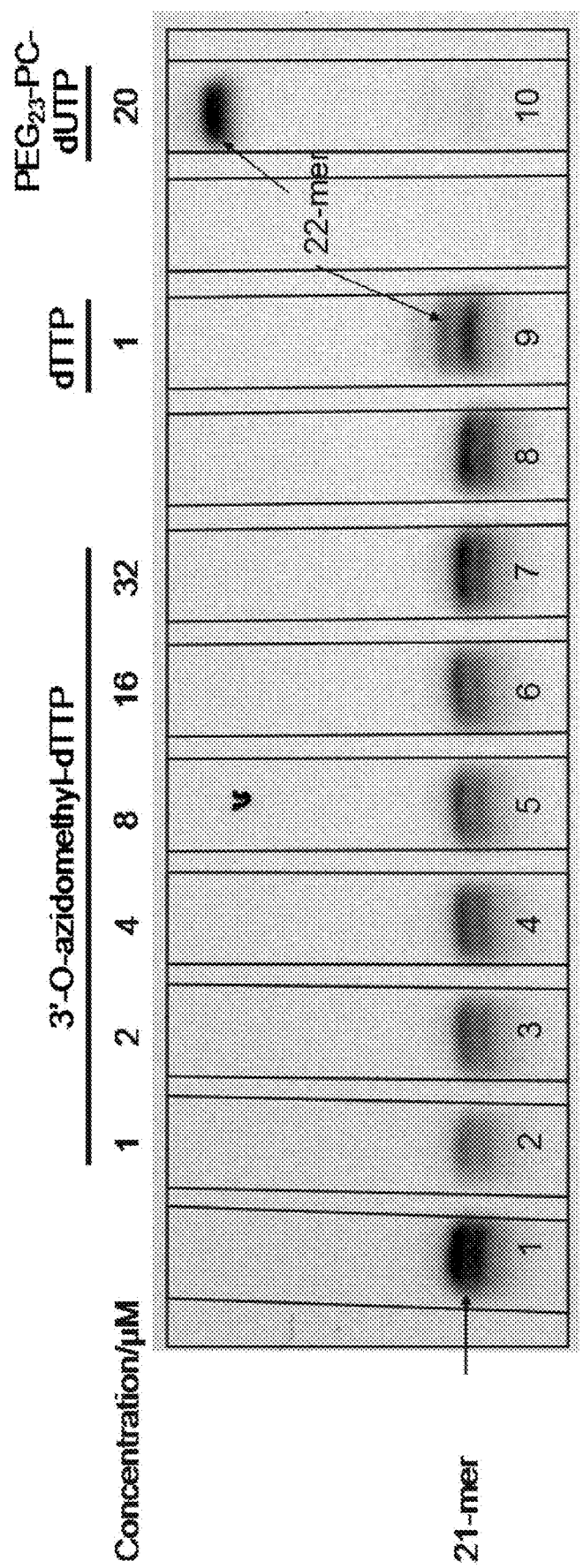
FIG. 4. TdT can incorporate base-modified nucleotides favorably, compared to 3' OH modified nucleotides.

To compare the incorporation of base-modified nucleotides and 3'-azidomethyl blocked dTTP, the incorporation of PEG$_{23}$-PC-dUTP and 3'-O-azidomethyl-dTTP by TdT was compared. By varying the concentration of 3'-O-azidomethyl-dTTP from 1 µM to 32 µM, TdT was unable to incorporate the 3' blocked nucleotides after 10 minutes of incubation (FIG. 4). On the other hand, base-modified nucleotides could be incorporated at a concentration of 20 µM (Lane 10, FIG. 4). This result shows that TdT can incorporate base-modified nucleotides favorably, compared to 3' OH modified nucleotides. FIG. 4. No incorporation of 3'-O-azidomethyl-dTTP nucleotide was observed after 10 minutes of incubation at 37° C. Lanes 1 and 8: 21-nt primer. Lanes 2-7: Increasing concentration (1-32 µM) of nucleotide. Lanes 9: Incorporation of 1 µM dTTP respectively as a positive control. Lane 10: Incorporation of PEG$_{23}$-PC-dUTP.

Figure 5:
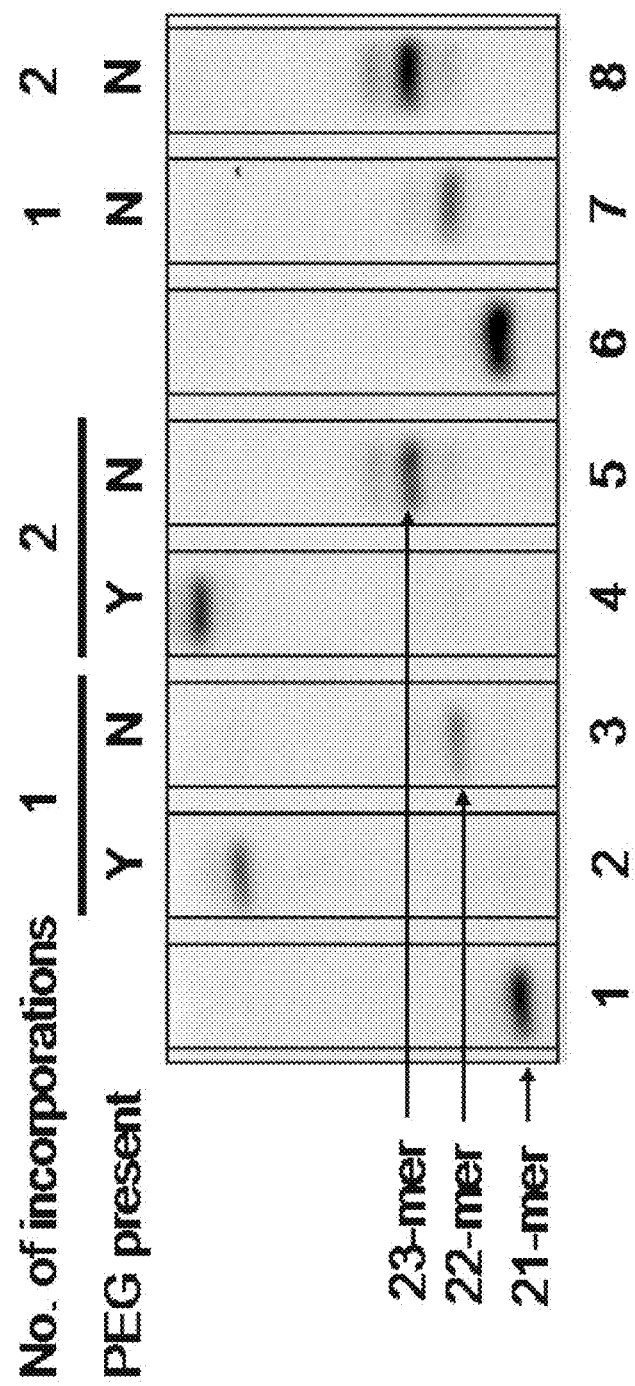
FIG. 5. Two cycles of incorporation and deprotection to demonstrate the feasibility of using compound 5 for enzymatic oligonucleotide synthesis.

With the optimized conditions in hand, the suitability of using PEG as a blocking group for DNA synthesis was tested with 2 cycles of incorporation and deprotection. Using compound 5, we incorporated the first nucleotide (lane 2), followed by the deactivation of TdT. Photo-induced cleavage of the PEG moiety gave the 22-nt product (+1 product, lane 3). The oligonucleotides were then purified to remove nucleotides, salts, and TdT. TdT incorporation of the second nucleotide (compound 5) gave the desired product (lane 4) followed by the removal of the PEG moiety to give the desired 23-nt oligo (+2 product, lane 5). The resulting 22-nt (+1 product) and 23-nt (+2 product) oligo were placed side by side to show the final product after each incorporation cycle (lanes 6-8). (FIG. 5). FIG. 5. Two cycles of incorporation and deprotection to demonstrate the feasibility of using compound 5 for enzymatic oligonucleotide synthesis. Lane 1: 21-nt oligo. Lane 2: Incorporation of the first nucleotide. Lane 3: Photocleavage of PEG moiety. Lane 4: Incorporation of the second nucleotide. Lane 5: Photocleavage of PEG moiety. Lane 6-8: Lanes 1, 3, and 5 respectively.

As the efficiency of the oligonucleotide clean-up kit is approximately 80%, the reduction of oligonucleotide concentration after clean-up would affect the yield of the second incorporation. This loss accounts for the difference in intensity observed in lanes 5 and 8. Through the use of solid support such as glass or magnetic beads, this loss can be reduced, producing cleaner products at each cycle.

With 7 minutes required for incorporation and 10 minutes for deprotection, together with the time required to purify oligonucleotides, the overall time taken for each cycle is approximately 30 minutes. The use of a higher-powered UV lamp or other cleavable chemistry such as disulfide linkage with faster kinetics rate could allow for more rapid cleavage of the PEG nucleobase block. The use of solid support also reduces the need for purification, further reducing the time required for each cycle.

With the success of using nucleobase-modified dUTP for single incorporation by TdT, the synthesis of modified dATP, dGTP, and dCTP (compounds 6-8) was carried out, providing yields ranging from 7% to 14% (Scheme 2). The nucleotides were then purified by high-performance liquid chromatography (HPLC) using a C18 column to give the products in high purity. As these compounds are highly unstable when exposed to light, these compounds were transferred to LightSafe microcentrifuge tubes immediately after purification for freeze-drying and storage.

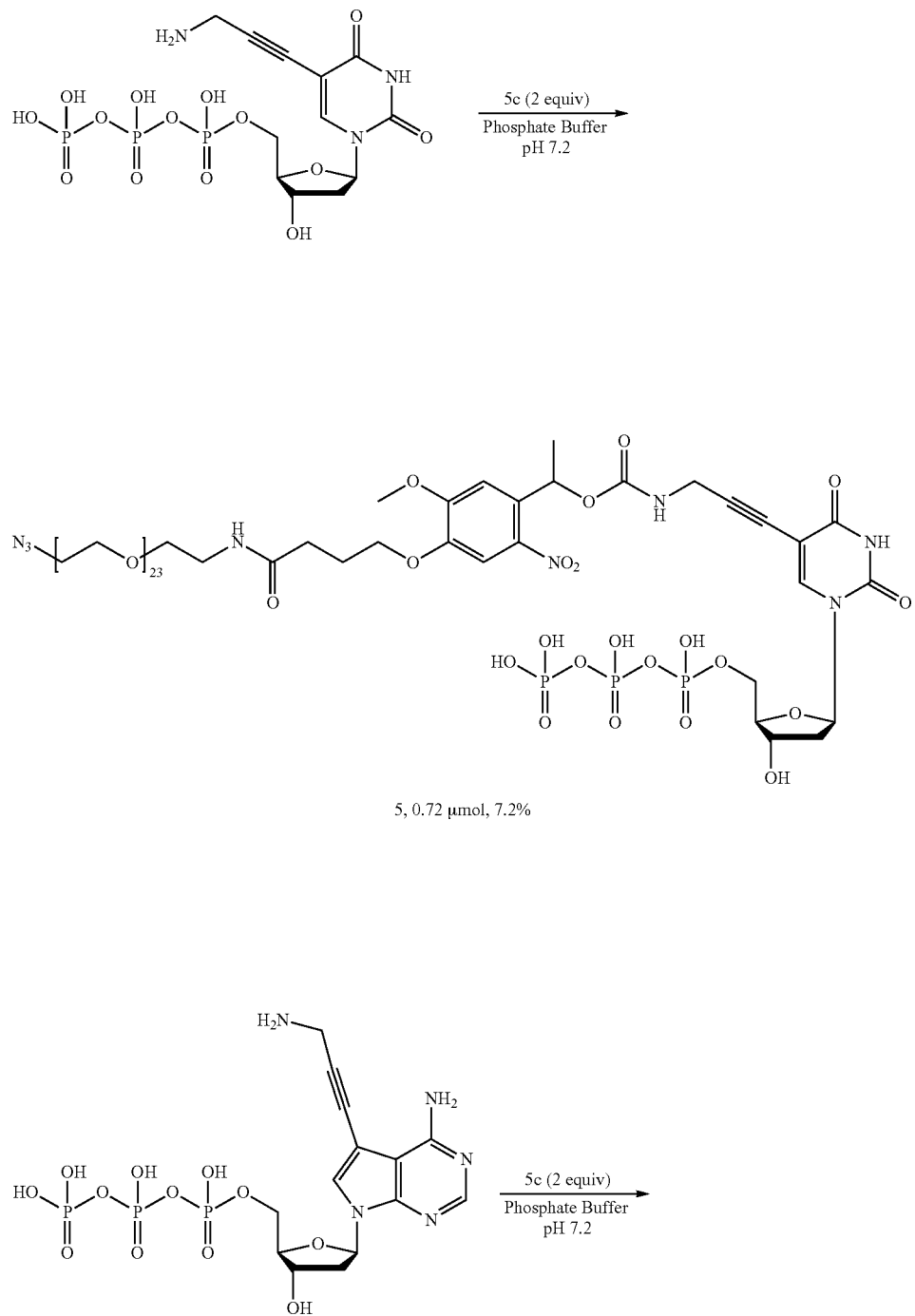

Scheme 2. Synthesis of compounds 5-8.

5, 0.72 μmol, 7.2%

-continued
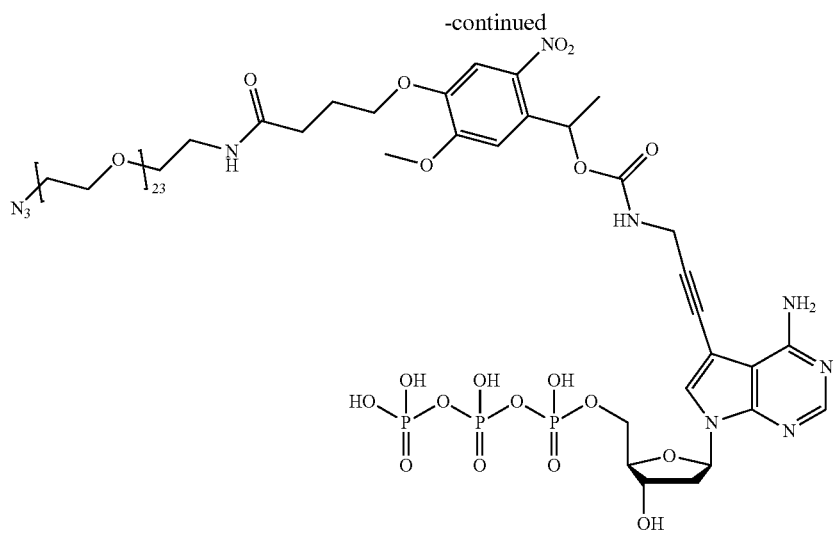
6, 0.81 μmol, 8.1%
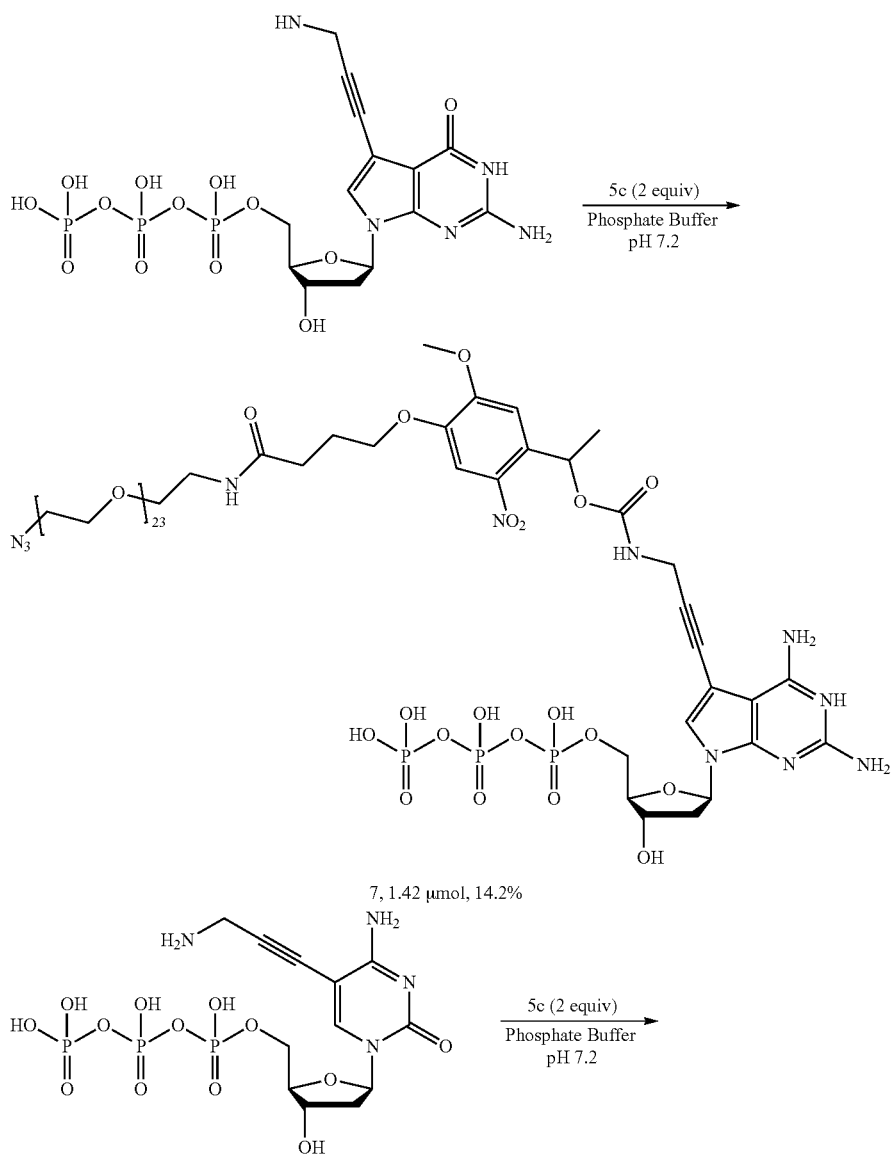
7, 1.42 μmol, 14.2%

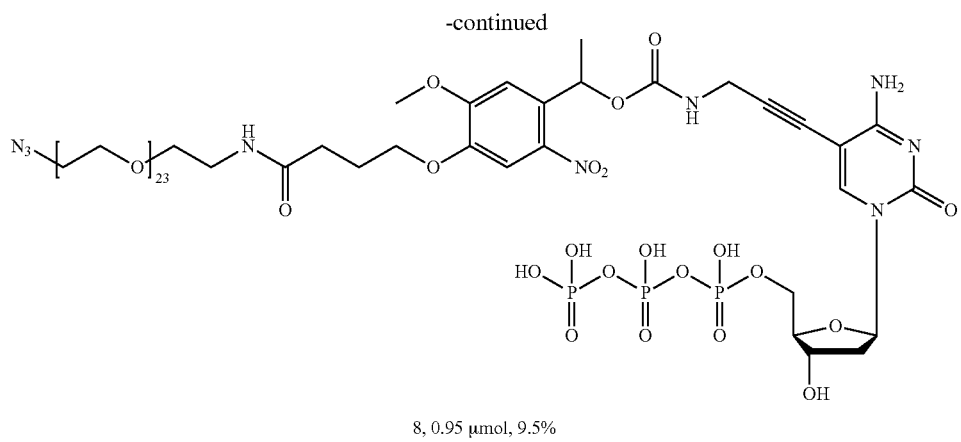

8, 0.95 µmol, 9.5%

Figure 6:
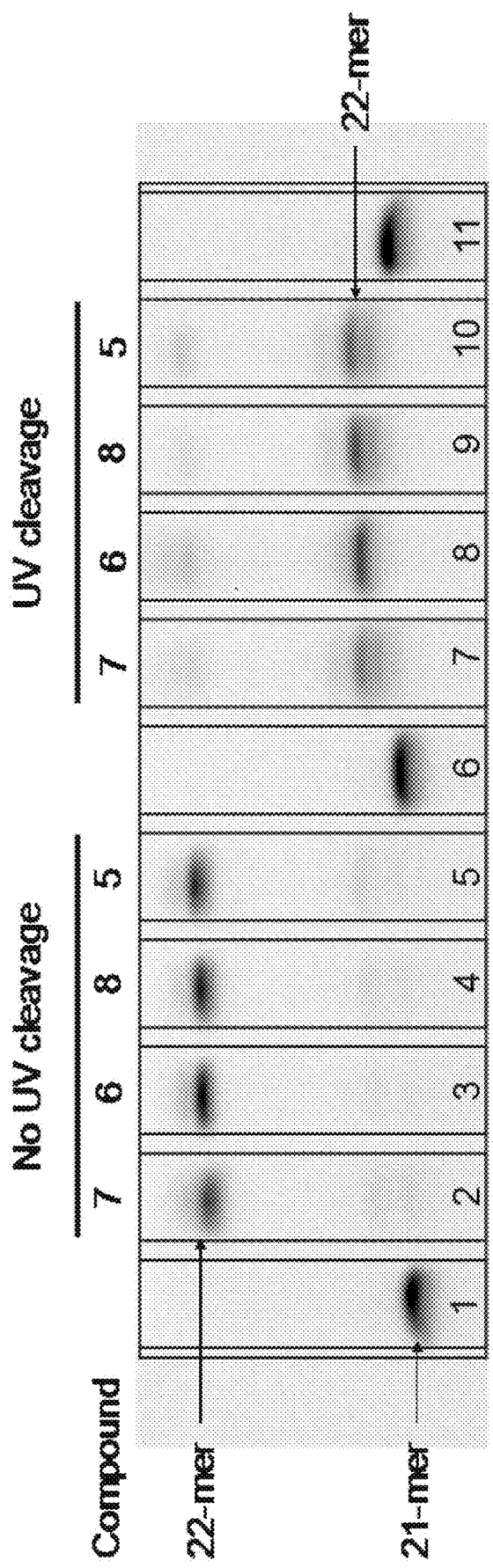
FIG. 6. Incorporation of nucleotides 5-8 by TdT.
Figure 7:
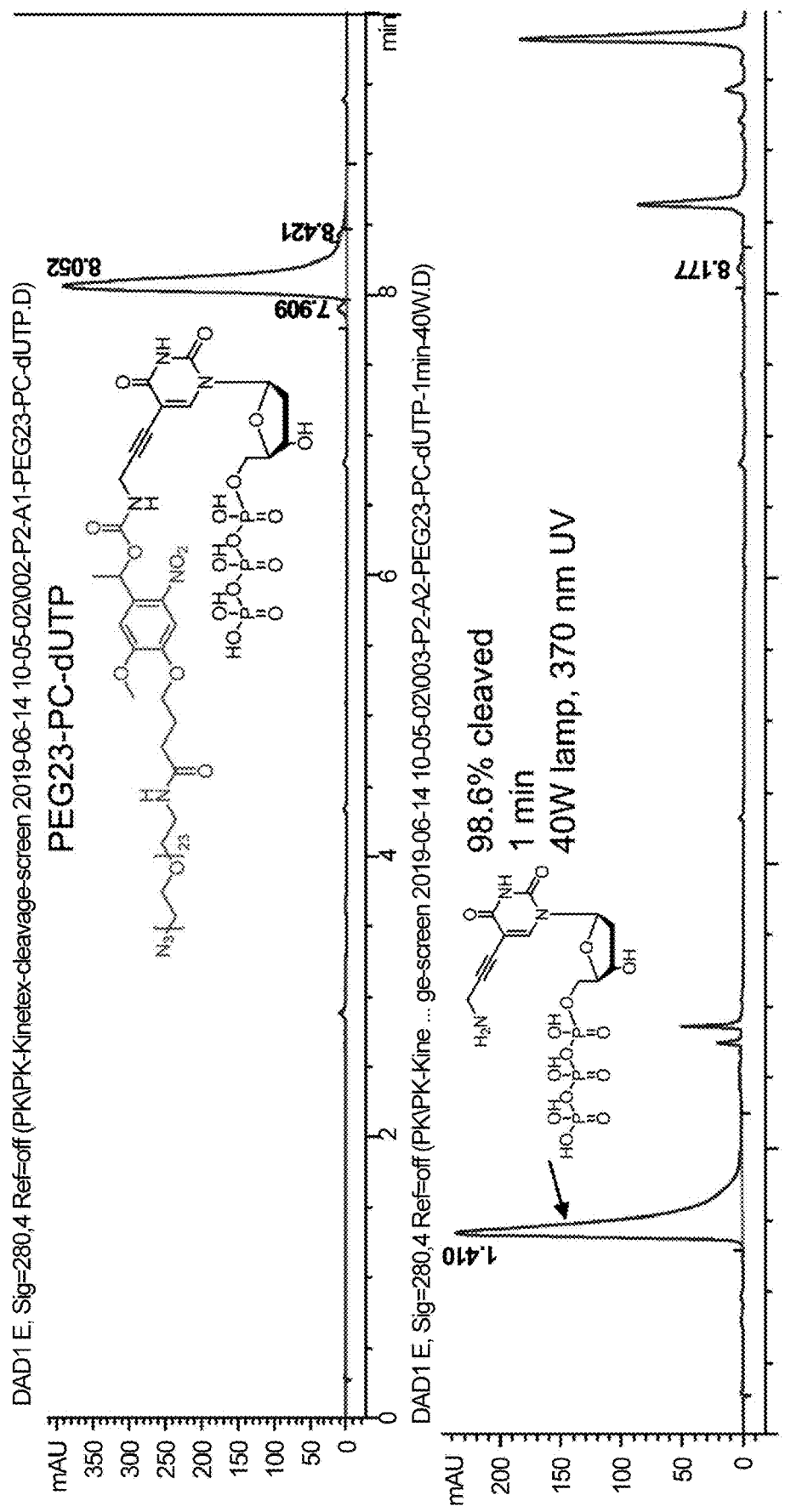
FIG. 7. UV photocleavage efficiency studies.
Figure 7:
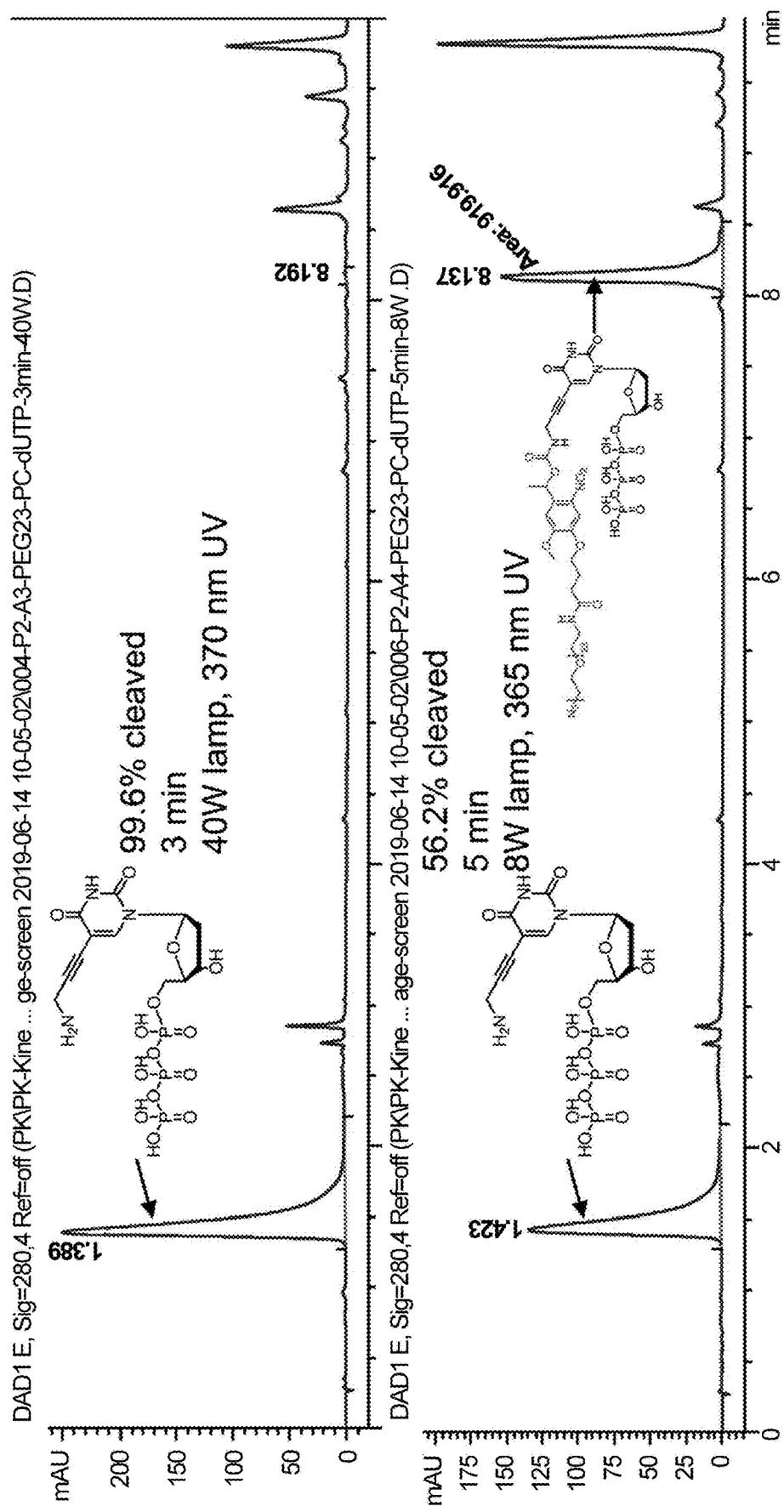

Compounds 5-8 were then used for TdT incorporation, using 80 µM of compound 5 and 40 µM of compounds 6-8. More than 88% incorporation yields were obtained for all the nucleotides (FIG. 6). The yields can be further improved by optimizing nucleotide concentration to achieve yields comparable to the phosphoramidite method. FIG. 1. Incorporation of nucleotides 5-8 by TdT. Lane 1, 6, and 11: 21-nt oligonucleotide. Lane 2-5: Incorporation of compounds 7, 6, 8, and 5 respectively. Lane 7-10: Photocleavage of products in lanes 2-5 respectively.

In order to reduce the time needed for photocleavage of the PEG chain, the cleavage efficiencies using various UV lamps were compared. A 40 W UV lamp was used in comparison with an 8 W UV lamp. Using 200 µM of protected nucleotides, the nucleotides were exposed to 40 W lamp at 370 nm ultraviolet light for 1-3 minutes and 8 W lamp at 365 nm ultraviolet light for 5 minutes. The nucleotides were then protected from light and analyzed. Using the 40 W lamp, more than 99% cleavage was observed after 1 minute and no more protected nucleotide was observed after 3 minutes of exposure. With the 8 W lamp, only 56% cleavage of the photolabile nucleotide was achieved. Thus, oligonucleotides with specific sequences can be synthesized with each cycle taking less than 10 mins, including 7 minutes of incorporation and 1 minute of photocleavage.

Through a systematic study of the base-blocking size requirement of nucleotides for single incorporation events, a discrete polyethylene glycol chain of 23 monomeric ethylene glycol units was found to be able to serve as a blocking group on the nucleobase of the nucleotide triphosphate to achieve single nucleotide incorporation with commercially available TdT. Upon the cleavage of the blocking group, subsequent incorporations was achieved.

Additional considerations include the presence of the propargylamino moiety, also known as the molecular scar, could slow incorporation efficiency. The incorporation of propargylamino-dUTP was slower compared to the incorporation of dTTP, the natural substrate of TdT (lanes 6 and 7, FIG. 2A). The time required for incorporation and removal of the PEG moiety can be reduced to bring down the overall time for each cycle. Finally, the yield of incorporation can be improved to match or even surpass the yield achieved by the phosphoramidite method for longer oligonucleotides synthesis. Other nucleobase chemistry can enable the removal of nucleobase modification faster without leaving a molecular scar.

TERMINOLOGY

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of nucleic acid synthesis comprising:
   (a) providing a nucleic acid and a plurality of nucleoside triphosphates, wherein each of the plurality of nucleoside triphosphates comprises a modified base comprising a photocleavable carbon chain moiety having a length of at least 60 Å;
   (b1) contacting (i) the nucleic acid and (ii) a first nucleoside triphosphate of the plurality of nucleoside triphosphates with a first terminal deoxynucleotidyl transferase (TdT) to generate a first modified nucleic acid comprising the nucleic acid incorporated with one first nucleotide comprising the modified base from the first nucleoside triphosphate;
   (c1) photocleaving the photocleavable carbon chain moiety of the modified base of the first nucleotide in the first modified nucleic acid to remove the photocleavable carbon chain moiety from the first modified nucleic acid;
   (b2) contacting (i) the first modified nucleic acid with the photocleavable carbon chain moiety of the modified base of the first nucleotide removed and (ii) a second nucleoside triphosphate of the plurality of nucleoside triphosphates with a second TdT to generate a second modified nucleic acid comprising the first modified nucleic acid incorporated with one second nucleotide comprising the modified base from the second nucleoside triphosphate; and
   (c2) photocleaving the photocleavable carbon chain moiety of the modified base of the second nucleotide in the second modified nucleic acid to remove the photocleavable carbon chain moiety from the second modified nucleic acid.

2. The method of claim 1, wherein the nucleic acid is attached to a solid support, the method further comprising: detaching the modified nucleic acid from the solid support.

3. The method of claim 1, wherein the modified base comprises a propargylamino group, an aminoallyl group, a propargylhydroxyl group or a combination thereof.

4. The method of claim 1, wherein the photocleavable carbon chain moiety comprises a saturated or unsaturated, substituted or unsubstituted, straight or branched carbon chain, and wherein the carbon chain has a length of at least 60 Å.

5. The method of claim 1, wherein the photocleavable carbon chain moiety comprises a plurality of repeat units.

6. The method of claim 5, wherein the plurality of repeating units comprises a polyethylene glycol (PEG).

7. The method of claim 5, wherein a number of the plurality of repeating units is at least 18.

8. The method of claim 1, wherein the photocleavable carbon chain moiety comprises an photocleavable moiety selected from a group consisting of a carbonyl group, an arylcarbonylmethyl group, a phenacyl group, an o-alkylphenacyl group, a p-hydroxyphenacyl group, a benzoin group, a benzyl group, a nitroaryl group, a nitrobenzyl group, an o-nitrobenzyl group, an o-nitro-2-phenethyloxycarbonyl group, an o-nitroanilide, a coumarin-4-ylmethyl group, an arylmethyl group, a coumaryl group, an o-hydroxyarylmethyl group, a metal-containing group, a pivaloyl group, an ester of a carboxylic acid, an arylsulfonyl group, a ketone group, a carbanion-mediated group, a sisyl group, a silicon-based group, a 2-hydroxycinnamyl group, an α-keto amide group, an α,β-unsaturated anilide, a methyl (phenyl)thiocarbamic acid group, a thiochromone S,S-dioxide group, 2-pyrrolidino-1,4-benzoquinone group, a triazine group, an arylmethyleneimino group, a xanthene group, a pyronin group, a 7-hydroxy-1,1-dimethylnaphthalenone group, a carboxylic acid group, a phosphate group, a phosphite group, a sulfate group, an acid group, an alcohol group, a thiol group, a N-oxide group, a phenol group, an amine group, a derivative of any of the proceeding, or a combination thereof.

9. The method of claim 1, wherein the first TdT and/or the second TdT comprises a recombinant TdT.

10. The method of claim 1, further comprising: removing or inactivating the first TdT after the step (b1) and before the step (c1); and removing or inactivating the second TdT after the step (b2) and before the step (c2).

11. The method of claim 1,
wherein the contacting in step (b1) is performed at about 16° C. to about 58° C., and
wherein the contacting step (b2) is performed at about 16° C. to about 58° C.

12. The method of claim 1,
wherein the first modified nucleic acid in step (b1) comprises at least 95% of the nucleic acid, and
wherein the second modified nucleic acid in step (b2) comprises at least 95% of the first modified nucleic acid.

13. The method of claim 1,
wherein at least 95% of the first modified nucleic acid in step (b1) comprises the first modified nucleic acid comprising the nucleic acid incorporated with a single first nucleotide from the first nucleoside triphosphate, and
wherein at least 95% of the second modified nucleic acid in step (b2) comprises the second modified nucleic acid comprising the first modified nucleic acid incorporated with a single second nucleotide from the second nucleoside triphosphate.

14. The method of claim 1,
wherein the photocleaving in step (c1) is performed with a first ultraviolet radiation, and
wherein the photocleaving in step (c2) is performed with a second ultraviolet radiation.

15. The method of claim 1, wherein the first radiation and/or the second radiation has a wattage of about 5 watts to about 20 watts.

16. The method of claim 1, wherein the photocleaving in the step (c1) and/or the step (c2) has an efficiency of at least 90%.

17. The method of claim 1, wherein the contacting in step (b1) and the contacting in step (b2) each is completed in about 7 minutes.

18. The method of claim 1, wherein the photocleaving in step (c1) and the photocleaving in step (c2) each is completed in about 1 minute.

19. The method of claim 1, further comprising: generating a reverse complement of the modified nucleic acid using a polymerase.

20. The method of claim 1, wherein the photocleavable carbon chain moiety comprises a polyether polymer.

21. The method of claim 20, wherein the polyether polymer comprises paraformaldehyde, polyethylene glycol (PEG), polypropylene glycol (PPG), polyalkylene glycol (PAG), polytetramethylene glycol (PTMG), or a combination thereof.

22. The method of claim 5, wherein a number of the plurality of repeating units is from about 18 to about 30.

* * * * *